United States Patent
Laury-Kleintop et al.

(10) Patent No.: US 9,879,092 B2
(45) Date of Patent: Jan. 30, 2018

(54) ANTI-RHOB ANTIBODIES

(75) Inventors: Lisa Laury-Kleintop, Ambler, PA (US); Laura Mandik-Nayak, Plymouth Meeting, PA (US); George C. Prendergast, Penn Valley, PA (US); James Duhadaway, Wilmington, DE (US)

(73) Assignee: Lankenau Institute for Medical Research, Wynnewood, PA (US)

( * ) Notice: Subject to any disclaimer, the term of this patent is extended or adjusted under 35 U.S.C. 154(b) by 501 days.

(21) Appl. No.: 14/237,706

(22) PCT Filed: Aug. 9, 2012

(86) PCT No.: PCT/US2012/050146
§ 371 (c)(1),
(2), (4) Date: Apr. 23, 2014

(87) PCT Pub. No.: WO2013/023059
PCT Pub. Date: Feb. 14, 2013

(65) Prior Publication Data
US 2014/0227279 A1 Aug. 14, 2014

Related U.S. Application Data

(60) Provisional application No. 61/522,009, filed on Aug. 10, 2011.

(51) Int. Cl.
*C07K 16/40* (2006.01)
*A61K 39/395* (2006.01)
*A61K 45/06* (2006.01)
*C07K 7/06* (2006.01)
*C07K 7/08* (2006.01)
*C07K 14/00* (2006.01)
*A61K 39/00* (2006.01)

(52) U.S. Cl.
CPC .......... *C07K 16/40* (2013.01); *A61K 39/3955* (2013.01); *A61K 45/06* (2013.01); *C07K 7/06* (2013.01); *C07K 7/08* (2013.01); *C07K 14/00* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 5,962,672 | A | 10/1999 | Coswert |
| 6,458,783 | B1 | 10/2002 | Williams et al. |
| 2005/0142103 | A1 | 6/2005 | Williams et al. |
| 2007/0213354 | A1 | 9/2007 | Dorr et al. |

FOREIGN PATENT DOCUMENTS

| | | |
|---|---|---|
| WO | 99/18951 | 4/1999 |
| WO | 2010/094490 | 8/2010 |

OTHER PUBLICATIONS

De Pascalis, R., et al. J. Immunol. 2002;169:3076-3084.*
Lamminmaki, U., et al. J. Biol. Chem. 2001;276(39):36687-36694.*
Bravo-Nuevo, et al., "RhoB Loss Prevents Streptozotocin-Induced Diabetes and Ameliorates Diabetic Complications in Mice," Am. J. Pathol. (2011) 178(1):245-252.
Wang, L., et al., "A Novel Strategy for Specifically Down-regulating Individual Rho GTPase Actvity in Tumor Cells," J. Biol. Chem. (2003) 278(45):44617-44625.
Santos-Bredariol, A.S., et al., "Small GTP-binding Protein RhoB is Expressed in Glial Cells in the Vertebrate Retina," J. Comparative Neurol. (2005) 494(5):976-985.
Zhao, D., et al., "Rho GTPases as Therapeutic Targets for the Treatment of Inflammatory Diseases," Exp. Opin. Therap. Targets (2003) 7(5):583-592.
Segain, J.P., et al., "Rho Kinase Blockade Prevents Inflammation via Nuclear Factor KappaB Inhibition: Evidence in Crohn'Disease and Experimental Colitis," Gastroenterol. (2003) 124(5):1180-1187.
Sun, X., et al., "The Selective Rho-kinase Inhibitor Fasudil is Protective and Therapeutic in Experimental Autoimmune Encephalomyelitis," J. Neuroimmunol. (2006) 180(1-2):126-134.
Greenwood, J., et al. "Lovastatin inhibits brain endothelial cell Rho-mediated lymphocyte migration and attenuates experimental autoimmune encephalomyelitis." FASEB J. May 2003;17(8):905-7. Epub Mar. 5, 2003.
Liu, J.P., et al. "A role for rhoB in the delamination of neural crest cells from the dorsal neural tube." Development Dec. 1998;125(24):5055-67.
Tillement, V., et al., "Phosphorylation of RhoB by CK1 impedes actin stress fiber organization and epidermal growth factor receptor stabilization," Experimental Cell Research (2008) 314:2811-2821.
Kitagawa, M., et al., "Composition for Treatment of Cancer," Abstract of WO2006/112401, Oct. 26, 2006.
Kazutake, T., et al., "Human ABH8 Protein, Gene for Encoding the Same, and Curative or Diagnostic Application of Them," Abstract of JP2008-178358, Aug. 7, 2008.

* cited by examiner

*Primary Examiner* — Gerald R Ewoldt
(74) *Attorney, Agent, or Firm* — Robert C. Netter, Jr.; Dann, Dorfman, Herrell & Skillman

(57) ABSTRACT

Anti-RhoB antibodies, compositions comprising the same, and methods for the treatment of autoimmune and inflammatory diseases using the anti-RhoB antibodies are disclosed.

7 Claims, 12 Drawing Sheets

MAAIRKKLVV VGDGACGKTC LLIVFSKDEF PEVYVPTVFE NYVADIEVDG
KQVELALWDT AGQEDYDRLR PLSYPDTDVI LMCFSVDSPD SLENIPEKWV
PEVKHFCPNV PIILVANKKD LRSDEHVRTE LARMKQEPVR TDDGRAMAVR
IQAYDYLECS AKTKEGVREV FETATRAALQ KRYGSQNGCI NCCKVL

Figure 3

```
                                                       FWR1
CCAGTTCCGAGCTCCAGATGACCCAGACTCCACTCTCCCTGCCTGTCAGTCTGGAGATCAA
   S  S  E  L  Q | M  T  Q  T  P  L  S  L  P  V  S  L  G  D  Q
                                   CDR1
GCCTCCATCTCTTGCAGATCAAGTCAGAGCCTTGTACACAGTAATGGAAACACCTATTTA
   A  S  I  S  C | R  S  Q  S  L  V  H  S  N  G  N  T  Y  L
                FWR2                                      CDR2
CATTGGTACCTGCAGAAGCCAGGCCAGTCTCCAAAGCTCCTGATCTACAAAGTTTCCAAC
   H | W  Y  L  Q  K  P  G  Q  S  P  K  L  L  I  Y | K  V  S  N
                                 FWR3
CGATTTTCTGGGGTCCCAGACAGGTTCAGTGGCAGTGGATCAGGGACAGATTTCACACTC
   R  F  S | G  V  P  D  R  F  S  G  S  G  S  G  T  D  F  T  L
                                                          CDR3
AAGATCAGCAGAGTGGAGGCTGAGGATCTGGGAGTTTATTTCTGCTCTCAAAGTACACAT
   K  I  S  R  V  E  A  E  D  L  G  V  Y  F  C | S  Q  S  T  H

GTTCCGtacacgttcggagggggaccaagctggaaataaaacgggctgatgctgcacca
   V  P  Y  T  F  G  G  G  T  K  L  E  I  K | R  A  D  A  A  P actgtatccatcttccaccatccagtgagcagttaacatctggaggtgcctcagtcgtg
   T  V  S  I  F  P  P  S  S  E  Q  L  T  S  G  G  A  S  V  V tgcttcttgaacaacttctaccccaaagacatcaatgtcaagtggaagattgatggcagt
   C  F  L  N  N  F  Y  P  K  D  I  N  V  K  W  K  I  D  G  S gaacgacaaaatggcgtcctgaacagttggactgatcaggacagcaaagacagcacctac
   E  R  Q  N  G  V  L  N  S  W  T  D  Q  D  S  K  D  S  T  Y agcatgagcagcaccctcacgttgaccaaggacgagtatgaacgacataacagctatacc
   S  M  S  S  T  L  T  L  T  K  D  E  Y  E  R  H  N  S  Y  T tgtgaggccactcacaagacatcaacttcacccattgtcaagagcttcaacaggaatgag
   C  E  A  T  H  K  T  S  T  S  P  I  V  K  S  F  N  R  N  E tgt
   C
```

Figure 9A

```
                                                       FWR1
TGAGGTGAAGCTGGTGGAGACTGGGGCTTCAGTGAAGTTGTCCTGCAAGGCTTCTGGCTAC
 E  V  K | L  V  E  T  G  A  S  V  K  L  S  C  K  A  S  G  Y
              CDR1                              FWR2
ACCTTCACC AGCTACTATATGTTC TGGGTGAAGCAGAGGCCTGGACATGGCCTTGAGTGG
 T  F  T | S  Y  Y  M  F | W  V  K  Q  R  P  G  H  G  L  E  W
                              CDR2
ATTGGG GGTTTAATCCTACCAATGGTGGTACTGACTTCAATGAGAAGTTCAAGAGC AAG
 I  G | G  F  N  P  T  N  G  G  T  D  F  N  E  K  F  K  S | K
                        FWR3
GCCACCCTGACTGTAGACAAGTCCTCCACCACAGCCTACATACAACTCAGCAGCCTGACA
 A  T  L  T  V  D  K  S  S  T  T  A  Y  I  Q  L  S  S  L  T
                                                    CDR3
TCTGAGGACTCTGCGGTCTATTACTGTAC ggatggtaacctctggggtcaaggaacctcg
 S  E  D  S  A  V  Y  Y  C  T  D  G  N  L  W  G  Q  G  T  S
gtcaccgtctcctcag ccaaaacgacacccccatctgtctatccactggcccctggatct
 V  T  V  S  S | A  K  T  T  P  P  S  V  Y  P  L  A  P  G  S
gctgcccaaactaactccatggtgaccctgggatgcctggtcaagggctatttccctgag
 A  A  Q  T  N  S  M  V  T  L  G  C  L  V  K  G  Y  F  P  E
ccagtgacagtgacctggaactctggatccctgtccagcggtgtgcacaccttcccagct
 P  V  T  V  T  W  N  S  G  S  L  S  S  G  V  H  T  F  P  A
gtcctgcagtctgacctctacactctgagcagctcagtgactgtccctccagcacctgg
 V  L  Q  S  D  L  Y  T  L  S  S  S  V  T  V  P  S  S  T  W
cccagcgagaccgtcacctgcaacgttgcccacccggccagcagcaccaaggtggacaag
 P  S  E  T  V  T  C  N  V  A  H  P  A  S  S  T  K  V  D  K
aaaattgtgcccagggattgtggttgtaagccttgcatatgtacagtcccagaagtatca
 K  I  V  P  R  D  C  G  C  K  P  C  I  C  T  V  P  E  V  S
tctgtcttcatcttccccccaaagcccaaggatgtgctcaccattactctgactcctaag
 S  V  F  I  F  P  P  K  P  K  D  V  L  T  I  T  L  T  P  K
gtcacgtgtgttgtggtagacatcagcaaggatgatcccgaggtccagttcagctggttt
 V  T  C  V  V  V  D  I  S  K  D  D  P  E  V  Q  F  S  W  F
gtagatgatgtggaggtgcacacagctcagacgcaaccccggggaggagcagttcaacagc
 V  D  D  V  E  V  H  T  A  Q  T  Q  P  R  E  E  Q  F  N  S
actttccgctcagtcagtgaacttcccatcatgcaccaggactggctcaatggcaaggag
 T  F  R  S  V  S  E  L  P  I  M  H  Q  D  W  L  N  G  K  E
ttcaaatgcagggtcaacagtgcagctttccctgcccccatcgagaaaaccatctccaaa
 F  K  C  R  V  N  S  A  A  F  P  A  P  I  E  K  T  I  S  K
accaaaggcagaccgaaggctccacaggtgtacaccattccacctcccaaggagcagatg
 T  K  G  R  P  K  A  P  Q  V  Y  T  I  P  P  P  K  E  Q  M
gccaaggataaagtcagtctgacctgcatgataacagacttcttccctgaagacattact
 A  K  D  K  V  S  L  T  C  M  I  T  D  F  F  P  E  D  I  T
gtggagtggcagtggaatgggcagccagcggagaactacaagaacactcagcccatcatg
 V  E  W  Q  W  N  G  Q  P  A  E  N  Y  K  N  T  Q  P  I  M
gacacagatggctcttacttcgtctacagcaagctcaatgtgcagaagagcaactgggag
 D  T  D  G  S  Y  F  V  Y  S  K  L  N  V  Q  K  S  N  W  E
gcaggaaatactttcacctgctctgtgttacatgagggcctgcacaaccaccatactgag
 A  G  N  T  F  T  C  S  V  L  H  E  G  L  H  N  H  H  T  E
aagagcctctcccactctcctggtaaa
 K  S  L  S  H  S  P  G  K
```

Figure 9B

```
                                          FWR1
ccAGTTCCGAGCTCCAGATGACCCAGACTCCAGCAATCATGTCTGCATCTCCAGGGGAGAAG
  S   S   E   L   Q | M   T   Q   T   P   A   I   M   S   A   S   P   G   E   K
                              CDR1
GTCACCATGACCTGCAGTGCCAGCTCAAGTGTAAGTTACATGCACTGGTACCAGCAGAAG
  V   T   M   T   C | S   A   S   S   S   V   S   Y   M   H | W   Y   Q   Q   K
FWR2                                       CDR2
CCAGGATCCTCGCCCAAACCCTGGATTTATGACACATCCAACCTGGCTTCTGGATTCCCT
  P   G   S   S   P   K   P   W   I   Y | D   T   S   N   L   A   S | G   F   P
                          FWR3
GCTCGCTTCAGTGGCAGTGGGTCTGGGACCTCTTACTCTCTCATAATCAGCAGCATGGAG
  A   R   F   S   G   S   G   S   G   T   S   Y   S   L   I   I   S   S   M   E

CDR3
GCTGAAGATGCTGCCACTTATTACTGCCATCAGCGGAGTAGTTACCCGtacacgttcgga
  A   E   D   A   A   T   Y   Y   C | H   Q   R   S   S   Y   P   Y   T   F   G gggggaccaagctggaaataaaacggctgatgctgcaccaactgtatccatcttccca
  G   G   T   K   L   E   I   K   R | A   D   A   A   P   T   V   S   I   F   P ccatccagtgagcagttaacatctggaggtgcctcagtcgtgtgcttcttgaacaacttc
  P   S   S   E   Q   L   T   S   G   G   A   S   V   V   C   F   L   N   N   F taccccaaagacatcaatgtcaagtggaagattgatggcagtgaacgacaaaatggcgtc
  Y   P   K   D   I   N   V   K   W   K   I   D   G   S   E   R   Q   N   G   V ctgaacagttggactgatcaggacagcaaagacagcacctacagcatgagcagcaccctc
  L   N   S   W   T   D   Q   D   S   K   D   S   T   Y   S   M   S   S   T   L acgttgaccaaggacgagtatgaacgacataacagctatacctgtgaggccactcacaag
  T   L   T   K   D   E   Y   E   R   H   N   S   Y   T   C   E   A   T   H   K acatcaacttcacccattgtcaagagcttcaacaggaatgagtgt
  T   S   T   S   P   I   V   K   S   F   N   R   N   E   C
```

Figure 10A

```
GAGGTGAAGCTGGTGGAGACWGGTGGAGGATTGGTGCAGCCTAAAGGGTCATTGAAACTC
 E   V   K   L   V   E   X   G   G   L   V   Q   P   K   G   S   L   K   L
FWR1                                   CDR1
TCATGTGCAGCCTCTGGATTCAACTTCAAT|ACCTACGCCATGAAC|TGGGTCCGCCAGGCT
 S   C   A   A   S   G   F   N   F   N | T   Y   A   M   N | W   V   R   Q   A
FWR2                                                            CDR2
CCAGGAAAGGGTTTGGAATGGGTTGCT|CGCATAAGAAGTAAAAGTAATAATTATGCAACA
 P   G   K   G   L   E   W   V   A | R   I   R   S   K   S   N   N   Y   A   T

TATTATGCCGATTCAGTGAAAGAC|AGATTCACCATCTCCAGAGATGATTCAGAAAACATG
 Y   Y   A   D   S   V   K   D | R   F   T   I   S   R   D   D   S   E   N   M
                      FWR3
CTCTATCTGCAAATGAACAACTTGAAAAACTGAGGACACAGCCATTTATTACTGTGTGAGA|
 L   Y   L   Q   M   N   N   L   K   T   E   D   T   A   T   Y   Y   C   V   R |
                  CDR3
ggggggtgg taaccttgactactggggccaaggcaccactctcacagtctcctca|gccaaa
 G   G   G   N   L   D   Y   W   G   Q   G   T   T   L   T   V   S   S | A   K
acaacagccccatcggtctatccactggccctgtgtgtggaggtacaactggctcctcg
 T   T   A   P   S   V   Y   P   L   A   P   V   C   G   G   T   T   G   S   S
gtgactctaggatgcctggtcaagggttatttccctgagccagtgaccttgacctggaac
 V   T   L   G   C   L   V   K   G   Y   F   P   E   P   V   T   L   T   W   N
tctggatccctgtccagtggtgtgcacaccttcccagctctcctgcagtctggcctctac
 S   G   S   L   S   S   G   V   H   T   F   P   A   L   L   Q   S   G   L   Y
accctcagcagctcagtgactgtaacctcgaacacctggcccagccagaccatcacctgc
 T   L   S   S   S   V   T   V   T   S   N   W   P   S   Q   T   I   T   C
aatgtggcccacccggcaagcagcaccaaagtggacaagaaaattgagcccagagtgccc
 N   V   A   H   P   A   S   S   T   K   V   D   K   K   I   E   P   R   V   P
ataacacagaaccctgtcctccactcaaagagtgtccccatgcgcagctccagacctc
 I   T   Q   N   P   C   P   P   L   K   E   C   P   P   C   A   A   P   D   L
ttgggtggaccatccgtcttcatcttccctccaaagatcaaggatgtactcatgatctcc
 L   G   G   P   S   V   F   I   F   P   P   K   I   K   D   V   L   M   I   S
ctgagccccatggtcacatgtgtggtggtggatgtgagcgaggatgacccagacgtccag
 L   S   P   M   V   T   C   V   V   V   D   V   S   E   D   D   P   D   V   Q
atcagctggtttgtgaacaacgtggaagtacacacagctcagacacaaacccatagagag
 I   S   W   F   V   N   N   V   E   V   H   T   A   Q   T   Q   T   H   R   E
gattacaacagtactctccgggtggtcagtgccctccccatccagcaccaggactggatg
 D   Y   N   S   T   L   R   V   V   S   A   L   P   I   Q   H   Q   D   W   M
agtggcaaggagttcaaatgcaaggtcaacaacagagccctcccatcccccatcgagaaa
 S   G   K   E   F   K   C   K   V   N   N   R   A   L   P   S   P   I   E   K
accatctcaaaacccagagggccagtaagagctccacaggtatatgtcttgcctccacca
 T   I   S   K   P   R   G   P   V   R   A   P   Q   V   Y   V   L   P   P   P
gcagaagagatgactaagaaagagttcagtctgacctgcatgatcacaggcttcttacct
 A   E   E   M   T   K   K   E   F   S   L   T   C   M   I   T   G   F   L   P
gccgaaattgctgtggactggaccagcaatgggcgtacagagcaaaactacaagaacacc
 A   E   I   A   V   D   W   T   S   N   G   R   T   E   Q   N   Y   K   N   T
gcaacagtcctggactctgatggttcttacttcatgtacagcaagctcagagtacaaaag
 A   T   V   L   D   S   D   G   S   Y   F   M   Y   S   K   L   R   V   Q   K
agcacttgggaagaggaagtcttttcgcctgctcagtggtccacgagggtctgcacaat
 S   T   W   E   R   G   S   L   F   A   C   S   V   V   H   E   G   L   H   N
caccttacgactaagaccttctcccggactccgggtaaa
 H   L   T   T   K   T   F   S   R   T   P   G   K
```

Figure 10B

SEQUENCE LISTING

```
<160> NUMBER OF SEQ ID NOS: 16

<210> SEQ ID NO 1
<211> LENGTH: 19
<212> TYPE: PRT
<213> ORGANISM: Artificial Sequence
<220> FEATURE:
<223> OTHER INFORMATION: Synthetic peptide

<400> SEQUENCE: 1

Arg Thr Asp Asp Gly Arg Ala Met Ala Val Arg Ile Gln Ala Tyr Asp
  1               5                  10                  15

Tyr Leu Glu

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide

<400> SEQUENCE: 2

Asp Asp Gly Arg Ala Met Ala Val Arg Ile Gln Ala Tyr
  1               5                  10

<210> SEQ ID NO 3
<211> LENGTH: 196
<212> TYPE: PRT
<213> ORGANISM: Homo sapiens

<400> SEQUENCE: 3

Met Ala Ala Ile Arg Lys Lys Leu Val Val Val Gly Asp Gly Ala Cys
  1               5                  10                  15

Gly Lys Thr Cys Leu Leu Ile Val Phe Ser Lys Asp Glu Phe Pro Glu
                 20                  25                  30

Val Tyr Val Pro Thr Val Phe Glu Asn Tyr Val Ala Asp Ile Glu Val
             35                  40                  45

Asp Gly Lys Gln Val Glu Leu Ala Leu Trp Asp Thr Ala Gly Gln Glu
         50                  55                  60

Asp Tyr Asp Arg Leu Arg Pro Leu Ser Tyr Pro Asp Thr Asp Val Ile
 65                  70                  75                  80

Leu Met Cys Phe Ser Val Asp Ser Pro Asp Ser Leu Glu Asn Ile Pro
                 85                  90                  95
```

```
Glu Lys Trp Val Pro Glu Val Lys His Phe Cys Pro Asn Val Pro Ile
            100                 105                 110

Ile Leu Val Ala Asn Lys Lys Asp Leu Arg Ser Asp Glu His Val Arg
            115                 120                 125

Thr Glu Leu Ala Arg Met Lys Gln Pro Val Arg Thr Asp Asp Gly
    130                 135                 140

Arg Ala Met Ala Val Arg Ile Gln Ala Tyr Asp Tyr Leu Glu Cys Ser
145                 150                 155                 160

Ala Lys Thr Lys Glu Gly Val Arg Glu Val Phe Glu Thr Ala Thr Arg
                165                 170                 175

Ala Ala Leu Gln Lys Arg Tyr Gly Ser Gln Asn Gly Cys Ile Asn Cys
            180                 185                 190

Cys Lys Val Leu
        195

<210> SEQ ID NO 4
<211> LENGTH: 193
<212> TYPE: PRT
<213> ORGANISM: Homo sapiens

<400> SEQUENCE: 4

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
            35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
            115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Ser Gly Cys Leu Ile
            180                 185                 190

Leu

<210> SEQ ID NO 5
<211> LENGTH: 82
<212> TYPE: PRT
<213> ORGANISM: Artificial Sequence
<220> FEATURE:
<223> OTHER INFORMATION: Synthetic peptide

<400> SEQUENCE: 5

Val Ala Asn Lys Lys Asp Leu Arg Ser Asp Glu His Val Arg Thr Glu
```

```
                1               5                  10                 15
Leu Ala Arg Met Lys Gln Glu Pro Val Arg Thr Asp Asp Gly Arg Ala
                  20                  25                  30

Met Ala Val Arg Ile Gln Ala Tyr Asp Tyr Leu Glu Cys Ser Ala Lys
                  35                  40                  45

Thr Lys Glu Gly Val Arg Glu Val Phe Glu Thr Ala Thr Arg Ala Ala
            50                  55                  60

Leu Gln Lys Arg Tyr Gly Ser Gln Asn Gly Cys Ile Asn Cys Cys Lys
65                  70                  75                  80

Val Leu

<210> SEQ ID NO 6
<211> LENGTH: 61
<212> TYPE: PRT
<213> ORGANISM: Artificial Sequence
<220> FEATURE:
<223> OTHER INFORMATION: Synthetic peptide

<400> SEQUENCE: 6

Lys Asp Leu Arg Ser Asp Glu His Val Arg Thr Glu Leu Ala Arg Met
1               5                   10                  15

Lys Gln Glu Pro Val Arg Thr Asp Asp Gly Arg Ala Met Ala Val Arg
                  20                  25                  30

Ile Gln Ala Tyr Asp Tyr Leu Glu Cys Ser Ala Lys Thr Lys Glu Gly
                  35                  40                  45

Val Arg Glu Val Phe Glu Thr Ala Thr Arg Ala Ala Leu
            50                  55                  60

<210> SEQ ID NO 7
<211> LENGTH: 74
<212> TYPE: PRT
<213> ORGANISM: Artificial Sequence
<220> FEATURE:
<223> OTHER INFORMATION: Synthetic peptide

<400> SEQUENCE: 7

Ser Asp Glu His Val Arg Thr Glu Leu Ala Arg Met Lys Gln Glu Pro
1               5                   10                  15

Val Arg Thr Asp Asp Gly Arg Ala Met Ala Val Arg Ile Gln Ala Tyr
                  20                  25                  30

Asp Tyr Leu Glu Cys Ser Ala Lys Thr Lys Glu Gly Val Arg Glu Val
                  35                  40                  45

Phe Glu Thr Ala Thr Arg Ala Ala Leu Gln Lys Arg Tyr Gly Ser Gln
            50                  55                  60

Asn Gly Cys Ile Asn Cys Cys Lys Val Leu
65                  70

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide

<400> SEQUENCE: 8

Ala Val Arg Ile Gln Ala Tyr Asp Tyr Leu Glu
1               5                   10

<210> SEQ ID NO 9
<211> LENGTH: 665
```

```
<212> TYPE: DNA
<213> ORGANISM: Artificial Sequence
<220> FEATURE:
<223> OTHER INFORMATION: light chain of 7F7

<400> SEQUENCE: 9
ccagttccga gctccagatg acccagactc cactctccct gcctgtcagt cttggagatc    60
aagcctccat ctcttgcaga tcaagtcaga gccttgtaca cagtaatgga aacacctatt   120
tacattggta cctgcagaag ccaggccagt ctccaaagct cctgatctac aaagtttcca   180
accgattttc tggggtccca gacaggttca gtggcagtgg atcagggaca gatttcacac   240
tcaagatcag cagagtggag gctgaggatc tgggagttta tttctgctct caaagtacac   300
atgttccgta cacgttcgga ggggggacca agctggaaat aaaacgggct gatgctgcac   360
caactgtatc catcttccca ccatccagtg agcagttaac atctggaggt gcctcagtcg   420
tgtgcttctt gaacaacttc taccccaaag acatcaatgt caagtggaag attgatggca   480
gtgaacgaca aaatggcgtc ctgaacagtt ggactgatca ggacagcaaa gacagcacct   540
acagcatgag cagcaccctc acgttgacca aggacgagta tgaacgacat aacagctata   600
cctgtgaggc cactcacaag acatcaactt cacccattgt caagagcttc aacaggaatg   660
agtgt                                                              665

<210> SEQ ID NO 10
<211> LENGTH: 221
<212> TYPE: PRT
<213> ORGANISM: Artificial Sequence
<220> FEATURE:
<223> OTHER INFORMATION: light chain of 7F7

<400> SEQUENCE: 10

Ser Ser Glu Leu Gln Met Thr Gln Thr Pro Leu Ser Leu Pro Val Ser
  1               5                  10                  15

Leu Gly Asp Gln Ala Ser Ile Ser Cys Arg Ser Ser Gln Ser Leu Val
             20                  25                  30

His Ser Asn Gly Asn Thr Tyr Leu His Trp Tyr Leu Gln Lys Pro Gly
         35                  40                  45

Gln Ser Pro Lys Leu Leu Ile Tyr Lys Val Ser Asn Arg Phe Ser Gly
     50                  55                  60

Val Pro Asp Arg Phe Ser Gly Ser Gly Ser Gly Thr Asp Phe Thr Leu
 65                  70                  75                  80

Lys Ile Ser Arg Val Glu Ala Glu Asp Leu Gly Val Tyr Phe Cys Ser
                 85                  90                  95

Gln Ser Thr His Val Pro Tyr Thr Phe Gly Gly Gly Thr Lys Leu Glu
            100                 105                 110

Ile Lys Arg Ala Asp Ala Ala Pro Thr Val Ser Ile Phe Pro Pro Ser
        115                 120                 125

Ser Glu Gln Leu Thr Ser Gly Gly Ala Ser Val Val Cys Phe Leu Asn
    130                 135                 140

Asn Phe Tyr Pro Lys Asp Ile Asn Val Lys Trp Lys Ile Asp Gly Ser
145                 150                 155                 160

Glu Arg Gln Asn Gly Val Leu Asn Ser Trp Thr Asp Gln Asp Ser Lys
                165                 170                 175

Asp Ser Thr Tyr Ser Met Ser Ser Thr Leu Thr Leu Thr Lys Asp Glu
            180                 185                 190

Tyr Glu Arg His Asn Ser Tyr Thr Cys Glu Ala Thr His Lys Thr Ser
        195                 200                 205
```

Thr Ser Pro Ile Val Lys Ser Phe Asn Arg Asn Glu Cys
    210                 215                 220

<210> SEQ ID NO 11
<211> LENGTH: 1288
<212> TYPE: DNA
<213> ORGANISM: Artificial Sequence
<220> FEATURE:
<223> OTHER INFORMATION: heavy chain of 7F7

<400> SEQUENCE: 11

```
tgaggtgaag ctggtggaga ctggggcttc agtgaagttg tcctgcaagg cttctggcta      60
caccttcacc agctactata tgttctgggt gaagcagagg cctggacatg gccttgagtg     120
gattgggggg tttaatccta ccaatggtgg tactgacttc aatgagaagt tcaagagcaa     180
ggccaccctg actgtagaca gtcctccac acagcctac atacaactca gcagcctgac      240
atctgaggac tctgcggtct attactgtac ggatggtaac ctctggggtc aaggaacctc     300
ggtcaccgtc tcctcagcca aaacgacacc cccatctgtc tatccactgg ccctggatc     360
tgctgcccaa actaactcca tggtgaccct gggatgcctg gtcaagggct atttccctga     420
gccagtgaca gtgacctgga actctggatc cctgtccagc ggtgtgcaca ccttcccagc     480
tgtcctgcag tctgacctct acactctgag cagctcagtg actgtcccct ccagcacctg     540
gcccagcgag accgtcacct gcaacgttgc cacccggcc agcagcacca aggtggacaa     600
gaaaattgtg cccagggatt gtggttgtaa gccttgcata tgtacagtcc cagaagtatc     660
atctgtcttc atcttccccc caaagcccaa ggatgtgctc accattactc tgactcctaa     720
ggtcacgtgt gttgtggtag acatcagcaa ggatgatccc gaggtccagt tcagctggtt     780
tgtagatgat gtgaggtgc acacagctca gacgcaaccc cgggaggagc agttcaacag     840
cactttccgc tcagtcagtg aacttcccat catgcaccag gactggctca atggcaagga     900
gttcaaatgc agggtcaaca gtgcagcttt ccctgccccc atcgagaaaa ccatctccaa     960
aaccaaaggc agaccgaagg ctccacaggt gtacaccatt ccacctccca aggagcagat    1020
ggccaaggat aaagtcagtc tgacctgcat gataacagac ttcttccctg aagacattac    1080
tgtggagtgg cagtggaatg ggcagccagc ggagaactac aagaacactc agcccatcat    1140
ggacacagat ggctcttact tcgtctacag caagctcaat gtgcagaaga gcaactggga    1200
ggcaggaaat actttcacct gctctgtgtt acatgagggc ctgcacaacc accatactga    1260
gaagagcctc tcccactctc ctggtaaa                                        1288
```

<210> SEQ ID NO 12
<211> LENGTH: 429
<212> TYPE: PRT
<213> ORGANISM: Artificial Sequence
<220> FEATURE:
<223> OTHER INFORMATION: heavy chain of 7F7

<400> SEQUENCE: 12

Glu Val Lys Leu Val Glu Thr Gly Ala Ser Val Lys Leu Ser Cys Lys
 1               5                  10                  15

Ala Ser Gly Tyr Thr Phe Thr Ser Tyr Tyr Met Phe Trp Val Lys Gln
            20                  25                  30

Arg Pro Gly His Gly Leu Glu Trp Ile Gly Gly Phe Asn Pro Thr Asn
        35                  40                  45

Gly Gly Thr Asp Phe Asn Glu Lys Phe Lys Ser Lys Ala Thr Leu Thr
    50                  55                  60

Val Asp Lys Ser Ser Thr Thr Ala Tyr Ile Gln Leu Ser Ser Leu Thr
65                  70                  75                  80

Ser Glu Asp Ser Ala Val Tyr Tyr Cys Thr Asp Gly Asn Leu Trp Gly
                85                  90                  95

Gln Gly Thr Ser Val Thr Val Ser Ser Ala Lys Thr Thr Pro Pro Ser
            100                 105                 110

Val Tyr Pro Leu Ala Pro Gly Ser Ala Ala Gln Thr Asn Ser Met Val
        115                 120                 125

Thr Leu Gly Cys Leu Val Lys Gly Tyr Phe Pro Glu Pro Val Thr Val
130                 135                 140

Thr Trp Asn Ser Gly Ser Leu Ser Ser Gly Val His Thr Phe Pro Ala
145                 150                 155                 160

Val Leu Gln Ser Asp Leu Tyr Thr Leu Ser Ser Val Thr Val Pro
                165                 170                 175

Ser Ser Thr Trp Pro Ser Glu Thr Val Thr Cys Asn Val Ala His Pro
            180                 185                 190

Ala Ser Ser Thr Lys Val Asp Lys Lys Ile Val Pro Arg Asp Cys Gly
        195                 200                 205

Cys Lys Pro Cys Ile Cys Thr Val Pro Glu Val Ser Ser Val Phe Ile
210                 215                 220

Phe Pro Pro Lys Pro Lys Asp Val Leu Thr Ile Thr Leu Thr Pro Lys
225                 230                 235                 240

Val Thr Cys Val Val Val Asp Ile Ser Lys Asp Asp Pro Glu Val Gln
                245                 250                 255

Phe Ser Trp Phe Val Asp Asp Val Glu Val His Thr Ala Gln Thr Gln
            260                 265                 270

Pro Arg Glu Glu Gln Phe Asn Ser Thr Phe Arg Ser Val Ser Glu Leu
        275                 280                 285

Pro Ile Met His Gln Asp Trp Leu Asn Gly Lys Glu Phe Lys Cys Arg
290                 295                 300

Val Asn Ser Ala Ala Phe Pro Ala Pro Ile Glu Lys Thr Ile Ser Lys
305                 310                 315                 320

Thr Lys Gly Arg Pro Lys Ala Pro Gln Val Tyr Thr Ile Pro Pro Pro
                325                 330                 335

Lys Glu Gln Met Ala Lys Asp Lys Val Ser Leu Thr Cys Met Ile Thr
            340                 345                 350

Asp Phe Phe Pro Glu Asp Ile Thr Val Glu Trp Gln Trp Asn Gly Gln
        355                 360                 365

Pro Ala Glu Asn Tyr Lys Asn Thr Gln Pro Ile Met Asp Thr Asp Gly
370                 375                 380

Ser Tyr Phe Val Tyr Ser Lys Leu Asn Val Gln Lys Ser Asn Trp Glu
385                 390                 395                 400

Ala Gly Asn Thr Phe Thr Cys Ser Val Leu His Glu Gly Leu His Asn
                405                 410                 415

His His Thr Glu Lys Ser Leu Ser His Ser Pro Gly Lys
            420                 425

<210> SEQ ID NO 13
<211> LENGTH: 647
<212> TYPE: DNA
<213> ORGANISM: Artificial Sequence
<220> FEATURE:
<223> OTHER INFORMATION: light chain of 9G5

<400> SEQUENCE: 13

```
ccagttccga gctccagatg acccagactc cagcaatcat gtctgcatct ccaggggaga      60
aggtcaccat gacctgcagt gccagctcaa gtgtaagtta catgcactgg taccagcaga     120
agccaggatc ctcgcccaaa ccctggattt atgacacatc caacctggct tctggattcc     180
ctgctcgctt cagtggcagt gggtctggga cctcttactc tctcataatc agcagcatgg     240
aggctgaaga tgctgccact tattactgcc atcagcggag tagttacccg tacacgttcg     300
gaggggggac caagctggaa ataaaacggg ctgatgctgc accaactgta tccatcttcc     360
caccatccag tgagcagtta acatctggag gtgcctcagt cgtgtgcttc ttgaacaact     420
tctaccccaa agacatcaat gtcaagtgga agattgatgg cagtgaacga caaaatggcg     480
tcctgaacag ttggactgat caggacagca agacagcac ctacagcatg agcagcaccc      540
tcacgttgac caaggacgag tatgaacgac ataacagcta tacctgtgag gccactcaca     600
agacatcaac ttcacccatt gtcaagagct tcaacaggaa tgagtgt                   647
```

<210> SEQ ID NO 14
<211> LENGTH: 215
<212> TYPE: PRT
<213> ORGANISM: Artificial Sequence
<220> FEATURE:
<223> OTHER INFORMATION: light chain of 9G5

<400> SEQUENCE: 14

```
Ser Ser Glu Leu Gln Met Thr Gln Thr Pro Ala Ile Met Ser Ala Ser
  1               5                  10                  15

Pro Gly Glu Lys Val Thr Met Thr Cys Ser Ala Ser Ser Val Ser
             20                  25                  30

Tyr Met His Trp Tyr Gln Gln Lys Pro Gly Ser Ser Pro Lys Pro Trp
         35                  40                  45

Ile Tyr Asp Thr Ser Asn Leu Ala Ser Gly Phe Pro Ala Arg Phe Ser
     50                  55                  60

Gly Ser Gly Ser Gly Thr Ser Tyr Ser Leu Ile Ile Ser Ser Met Glu
 65                  70                  75                  80

Ala Glu Asp Ala Ala Thr Tyr Tyr Cys His Gln Arg Ser Ser Tyr Pro
                 85                  90                  95

Tyr Thr Phe Gly Gly Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215
```

<210> SEQ ID NO 15
<211> LENGTH: 1359
<212> TYPE: DNA

-continued

<213> ORGANISM: Artificial Sequence
<220> FEATURE:
<223> OTHER INFORMATION: heavy chain of 9G5

<400> SEQUENCE: 15

```
gaggtgaagc tggtggagac wggtggagga ttggtgcagc ctaaagggtc attgaaactc      60
tcatgtgcag cctctggatt caacttcaat acctacgcca tgaactgggt ccgccaggct     120
ccaggaaagg gtttgaatg ggttgctcgc ataagaagta aagtaataa ttatgcaaca       180
tattatgccg attcagtgaa agacagattc accatctcca gagatgattc agaaaacatg     240
ctctatctgc aaatgaacaa cttgaaaact gaggacacag ccatttatta ctgtgtgaga     300
ggggtggta accttgacta ctggggccaa ggcaccactc tcacagtctc ctcagccaaa      360
acaacagccc catcggtcta tccactggcc cctgtgtgtg aggtacaac tggctcctcg      420
gtgactctag gatgcctggt caagggttat ttccctgagc cagtgacctt gacctggaac     480
tctggatccc tgtccagtgg tgtgcacacc ttcccagctc tcctgcagtc tggcctctac     540
accctcagca gctcagtgac tgtaacctcg aacacctggc ccagccagac catcacctgc     600
aatgtggccc acccggcaag cagcaccaaa gtggacaaga aaattgagcc cagagtgccc     660
ataacacaga acccctgtcc tccactcaaa gagtgtcccc catgcgcagc tccagacctc     720
ttgggtggac catccgtctt catcttccct ccaaagatca aggatgtact catgatctcc     780
ctgagcccca tggtcacatg tgtggtggtg gatgtgagcg aggatgaccc agacgtccag     840
atcagctggt ttgtgaacaa cgtggaagta cacacagctc agacacaaac ccatagagag     900
gattacaaca gtactctccg ggtggtcagt gccctcccca tccagcacca ggactggatg     960
agtggcaagg agttcaaatg caaggtcaac aacagagccc tcccatcccc catcgagaaa    1020
accatctcaa aacccagagg gccagtaaga gctccacagg tatatgtctt gcctccacca    1080
gcagaagaga tgactaagaa agagttcagt ctgacctgca tgatcacagg cttcttacct    1140
gccgaaattg ctgtggactg gaccagcaat gggcgtacag agcaaaacta caagaacacc    1200
gcaacagtcc tggactctga tggttcttac ttcatgtaca gcaagctcag agtacaaaag    1260
agcacttggg aaagaggaag tcttttcgcc tgctcagtgg tccacgaggg tctgcacaat    1320
caccttacga ctaagacctt ctcccggact ccgggtaaa                           1359
```

<210> SEQ ID NO 16
<211> LENGTH: 453
<212> TYPE: PRT
<213> ORGANISM: Artificial Sequence
<220> FEATURE:
<223> OTHER INFORMATION: heavy chain of 9G5

<400> SEQUENCE: 16

```
Glu Val Lys Leu Val Glu Thr Gly Gly Gly Leu Val Gln Pro Lys Gly
  1               5                  10                  15

Ser Leu Lys Leu Ser Cys Ala Ala Ser Gly Phe Asn Phe Asn Thr Tyr
             20                  25                  30

Ala Met Asn Trp Val Arg Gln Ala Pro Gly Lys Gly Leu Glu Trp Val
         35                  40                  45

Ala Arg Ile Arg Ser Lys Ser Asn Asn Tyr Ala Thr Tyr Tyr Ala Asp
     50                  55                  60

Ser Val Lys Asp Arg Phe Thr Ile Ser Arg Asp Asp Ser Glu Asn Met
 65                  70                  75                  80

Leu Tyr Leu Gln Met Asn Asn Leu Lys Thr Glu Asp Thr Ala Ile Tyr
                 85                  90                  95
```

-continued

```
Tyr Cys Val Arg Gly Gly Gly Asn Leu Asp Tyr Trp Gly Gln Gly Thr
            100                 105                 110

Thr Leu Thr Val Ser Ser Ala Lys Thr Thr Ala Pro Ser Val Tyr Pro
            115                 120                 125

Leu Ala Pro Val Cys Gly Gly Thr Thr Gly Ser Ser Val Thr Leu Gly
            130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Leu Leu Gln
                165                 170                 175

Ser Gly Leu Tyr Thr Leu Ser Ser Ser Val Thr Val Thr Ser Asn Thr
                180                 185                 190

Trp Pro Ser Gln Thr Ile Thr Cys Asn Val Ala His Pro Ala Ser Ser
            195                 200                 205

Thr Lys Val Asp Lys Lys Ile Glu Pro Arg Val Pro Ile Thr Gln Asn
            210                 215                 220

Pro Cys Pro Pro Leu Lys Glu Cys Pro Pro Cys Ala Ala Pro Asp Leu
225                 230                 235                 240

Leu Gly Gly Pro Ser Val Phe Ile Phe Pro Pro Lys Ile Lys Asp Val
                245                 250                 255

Leu Met Ile Ser Leu Ser Pro Met Val Thr Cys Val Val Val Asp Val
                260                 265                 270

Ser Glu Asp Asp Pro Asp Val Gln Ile Ser Trp Phe Val Asn Asn Val
                275                 280                 285

Glu Val His Thr Ala Gln Thr Gln Thr His Arg Glu Asp Tyr Asn Ser
            290                 295                 300

Thr Leu Arg Val Val Ser Ala Leu Pro Ile Gln His Gln Asp Trp Met
305                 310                 315                 320

Ser Gly Lys Glu Phe Lys Cys Lys Val Asn Asn Arg Ala Leu Pro Ser
                325                 330                 335

Pro Ile Glu Lys Thr Ile Ser Lys Pro Arg Gly Pro Val Arg Ala Pro
                340                 345                 350

Gln Val Tyr Val Leu Pro Pro Ala Glu Glu Met Thr Lys Lys Glu
            355                 360                 365

Phe Ser Leu Thr Cys Met Ile Thr Gly Phe Leu Pro Ala Glu Ile Ala
            370                 375                 380

Val Asp Trp Thr Ser Asn Gly Arg Thr Glu Gln Asn Tyr Lys Asn Thr
385                 390                 395                 400

Ala Thr Val Leu Asp Ser Asp Gly Ser Tyr Phe Met Tyr Ser Lys Leu
                405                 410                 415

Arg Val Gln Lys Ser Thr Trp Glu Arg Gly Ser Leu Phe Ala Cys Ser
            420                 425                 430

Val Val His Glu Gly Leu His Asn His Leu Thr Thr Lys Thr Phe Ser
            435                 440                 445

Arg Thr Pro Gly Lys
            450
```

ANTI-RHOB ANTIBODIES

This application is a § 371 application of PCT/US2012/050146, filed Aug. 9, 2012, which claims priority under 35 U.S.C. § 119(e) to U.S. Provisional Patent Application No. 61/522,009, filed Aug. 10, 2011. The foregoing applications are incorporated by reference herein.

FIELD OF THE INVENTION

This invention relates generally to the field of autoimmune and inflammatory diseases. Specifically, the invention provides novel compositions and methods for the treatment of diseases that have an autoimmune and/or inflammatory component in their pathology.

BACKGROUND OF THE INVENTION

Autoimmune disease occurs when an organism fails to recognize its own constituent parts as "self," thereby resulting in an immune response against its own cells and tissues. In other words, the body actually attacks its own cells. The immune system mistakes some part of the body as a pathogen and attacks it. Current treatments for autoimmune diseases typically include immunosuppression and/or symptomatic treatment with non-disease modifying anti-inflammatories in order to decreases the damage of the aberrant immune response. However, there is a need in the art for methods and compositions for inhibiting and/or delaying the onset of pathology associated with autoimmune disorders.

SUMMARY OF THE INVENTION

In accordance with one aspect of the instant invention, methods for inhibiting, treating, and/or preventing the onset of an autoimmune and/or inflammatory disease and/or diseases that have an autoimmune and/or inflammatory component in their pathology in patients in need thereof are provided. The methods comprise the administration of at least one RhoB inhibitor. In a particular embodiment, the RhoB inhibitor is an antibody or antibody fragment immunologically specific for RhoB or a peptide fragment thereof. In a particular embodiment, the RhoB inhibitor is a structurally related or derived small molecule of the antibody, antibody fragment, peptide fragment or chemical or biologically mimetic of the antibodies' CDR regions and epitopes recognized by the CDRs. In a particular embodiment, the RhoB inhibitor is a RhoB peptide. In a particular embodiment, the methods comprise the administration of a composition comprising at least one RhoB peptide and/or antibody or antibody fragment immunologically specific for RhoB or a peptide fragment thereof and at least one pharmaceutically acceptable carrier. In a particular embodiment, the methods further comprise the administration of at least one anti-inflammatory agent and/or immunosuppressant concurrently and/or sequentially with the at least one RhoB inhibitor (e.g., an antibody or antibody fragment immunologically specific for RhoB or a peptide fragment thereof).

Compositions for the inhibition, treatment, and/or prevention of inflammatory or autoimmune disease are also provided. The compositions comprise at least one RhoB inhibitor and at least one pharmaceutically acceptable carrier. In a particular embodiment, the RhoB inhibitor is antibody or antibody fragment immunologically specific for RhoB or a peptide fragment thereof. In a particular embodiment, the RhoB inhibitor is a RhoB peptide. In another embodiment, the composition further comprises at least one anti-inflammatory compound and/or at least one immunosuppressive agent.

The instant invention also provides anti-RhoB antibodies, RhoB peptide (e.g., for the generation of antibodies), or structurally related or derived small molecules of the antibody, antibody fragment, peptide fragment or chemical or biologically mimetic of the antibodies' CDR regions and epitopes recognized by the CDRs, and compositions comprising the same.

In accordance with one aspect of the instant invention, methods for inhibiting, treating, and/or preventing a condition or disorder associated with increased levels of immunoglobulin in the blood serum (e.g., hypergammaglobulinemia or monoclonal gammopathy of undetermined significance) in patients in need thereof are provided. The methods comprise the administration of at least one RhoB inhibitor as described herein.

BRIEF DESCRIPTION OF THE DRAWINGS

FIG. 3 provides the amino acid sequence of human RhoB (SEQ ID NO: 3). Underlined sequence is Peptide 1 (SEQ ID NO: 1).

FIG. 9A provides the nucleotide (SEQ ID NO: 9) and amino acid (SEQ ID NO: 10) sequences of the light chain of 7F7. FIG. 9B provides the nucleotide (SEQ ID NO: 11) and amino acid (SEQ ID NO: 12) sequences of the heavy chain of 7F7. Vertical lines represent borders between domains. Bold—variable region (V); underlined—joining region (J); italics—diversity region (D); FWR—framework region; CDR—complementarity determining region.

FIG. 10A provides the nucleotide (SEQ ID NO: 13) and amino acid (SEQ ID NO: 14) sequences of the light chain of 9G5. FIG. 10B provides the nucleotide (SEQ ID NO: 15) and amino acid (SEQ ID NO: 16) sequences of the heavy chain of 9G5. Vertical lines represent borders between domains. Bold—variable region (V); underlined—joining region (J); italics—diversity region (D); FWR framework region; CDR—complementarity determining region.

DETAILED DESCRIPTION OF THE INVENTION

Figure 1:
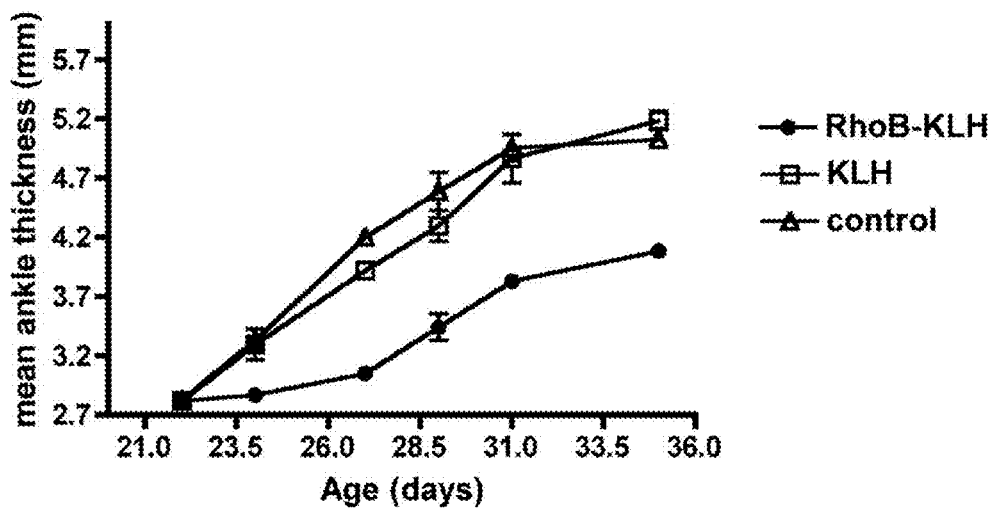
FIG. 1 is a graph of the mean ankle thickness over time of K/BxN mice which were treated with anti-RhoB-peptide serum, anti-KLH serum, or carrier alone.

Stable hybridomas that produce a monoclonal antibody directed against RhoB have been difficult to generate and maintain. While attempting to obtain a hybridoma, it has been observed that the most relevant hybridomas either die or stop secreting the anti-RhoB antibody. This observation led to the hypothesis that an antibody against RhoB might inhibit antibody production in B cells. Herein, it is shown that antibodies against RhoB can inhibit the secretion of immunoglobulins from stimulated murine B cells. Further, it is shown herein that antibodies against RhoB delay the onset and attenuate the course of arthritis in an animal model of autoantibody-driven rheumatoid arthritis (RA). Diseases or disease symptoms that are the result of autoantibody production would benefit from a therapy that blocks or attenuates antibody production.

The administration of the anti-RhoB antibody may be similar to other antibody-based therapies which are tolerable despite their non-targeted aspect for disease treatment. Examples include, but are not limited to, the antibody therapies anti-TNF (infliximab, adalimumab, etanercept), anti-CD20 (rituximab), and anti-BLyS (belimumab). These therapies generally blunt inflammation or eradicate B cells or B cell function. For patients that poorly tolerate these therapies, the anti-RhoB antibody provides another therapeutic option.

The administration of RhoB antibodies will likely have low or no toxicity or side-effects. Notably, mice that are genetically deficient for RhoB are normal and lack evident immune deficiencies, including deficiencies in B cell responses to antigen stimulation or IgG memory formation. While RhoB deficient mice generate a normal IgG antibody response, they did exhibit a mildly reduced IgM secondary response. Thus, the anti-RhoB technology appears to retard abnormal B cell function in the production of autoimmune antibodies, but it does not disrupt normal B cell function after canonical antigenic challenge. Notably, RhoB is a stress response protein with a short half-life, so it is likely quickly depleted as well as functionally impaired by a specific antibody blockade.

RhoB is an intracellular protein. Without being bound by theory, the anti-RhoB antibody may enter cells through the Fc receptor. As such, this would result in reduced toxicity or side-effects since only cells expressing the Fc receptor may be susceptible to anti-RhoB antibody therapy. Similarly, toxicity should also be lower than non-targeted immunomodulatory agents such as dexamethasone, prednisone, or thalidomide, which are used in clinic presently.

While the instant invention discloses anti-RhoB antibody therapy, other inhibitors of RhoB (e.g., RhoB activity and/or expression) may be used in place or in coordination with the anti-RhoB antibodies. For example, nucleic acid molecules which inhibit RhoB expression may be used such as siRNA and antisense molecules. Micro-RNA-21 has been shown to reduce RhoB expression (Sabatel et al. PLoS One (2011) 6:e16979). Additionally, RhoB peptide sequences identified herein or structurally related small molecules based on the peptide sequences or CDRs which interact with corresponding epitopes on RhoB may also serve as inhibitors of RhoB activity, particularly when coupled to appropriate delivery systems.

Antibody-mediated disruption of RhoB retards, inhibits, and/or blunts inflammatory cellular responses that involve B cells. As mentioned above, antibodies against RhoB can be used to alleviate diseases or disease symptoms that are the result of autoantibody production and/or secretion. However, specific RhoB targeted therapeutics (e.g., delivered via an intracellular delivery systems for macromolecules (e.g., the variable region of an IgG molecule)) may be designed that arrest or re-direct intracellular inflammatory signals that are organized by B cells. In this manner, the anti-RhoB therapy will work in cell types that contribute to chronic inflammation, such as mesenchymal cells (endothelial cells, myofibroblasts, smooth muscle cells, monocyte/macrophages) that are thought to contribute to the development of cardiovascular disease (CVD), cancer, diabetes or other major diseases that may be directly or indirectly supported by an inflammatory tissue environment.

In CVD, preclinical studies have shown that RhoB is regulated by statins and there is clinical evidence that the "non-cholesterol lowering" effect of statins can be attributed to anti-inflammatory actions. Thus, anti-RhoB therapies may be used to limit atherosclerosis or be combined with statins or other anti-inflammatory therapeutics as new therapeutic options. In other inflammatory tissue settings, anti-RhoB can also inhibit the inflammatory response of fibroblasts. As such, anti-RhoB therapy can blunt fibrotic responses that contribute to tissue scarring, such as in skin, liver or heart.

With regard to diabetes, it has been shown that autoantibodies were required for the activation of disease causing T cells (Harbers et al. (2007) J. Clin. Invest., 117:1361-1369). Accordingly, the development of approaches to prevent autoantibodies from activating T cells (e.g., by reducing or inhibiting autoantibodies) would prevent or treat autoimmune disease. Notably, it has been demonstrated that antibodies specific for CD20 can reduce the onset of diabetes by depleting a subset of B cells (Hu et al. (2007) J. Clin. Invest., 117:3857-3867). In addition to diabetes, antibody mediated treatment of other autoimmune diseases have been demonstrated. For example, it has been shown that antibodies against the sphingosine 1-phosphate receptor reduced colitis in a mouse model (Liao et al. (2009) FASEB J., 23:1786-96).

As stated hereinabove, the instant invention provides compositions and methods for the inhibition, treatment, and/or prevention of autoimmune diseases and/or inflammatory diseases. In a particular embodiment, the autoimmune diseases or inflammatory diseases to be treated by the methods of the invention are those in which B-cells are implicated in the pathophysiology and/or the symptoms of disease. Such autoimmune diseases and inflammatory disease may also be referred to as B-cell mediated autoimmune diseases or inflammatory disease. B-cells have been implicated in playing a role in the pathophysiology of a variety of autoimmune or inflammatory diseases (see, e.g., Browning, J. L. (2006) Nat. Rev. Drug Discov., 5:564-576).

As used herein, the term "autoimmune disease" refers to the presence of an autoimmune response (an immune response directed against an auto- or self-antigen) in a subject. Autoimmune diseases include diseases caused by a breakdown of self-tolerance such that the adaptive immune system responds to self antigens and mediates cell and tissue damage. In a particular embodiment, autoimmune diseases are characterized as being a result of, at least in part, a humoral immune response.

Examples of autoimmune disease include, without limitation, acute disseminated encephalomyelitis (ADEM), acute necrotizing hemorrhagic leukoencephalitis, Addison's disease, agammaglobulinemia, allergic asthma, allergic rhinitis, alopecia areata, amyloidosis, ankylosing spondylitis, antibody-mediated transplantation rejection, anti-GBM/Anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura (ATP), autoimmune thyroid disease, autoimmune urticaria, axonal & neuronal neuropathies, Balo disease, Behcet's disease, bullous pemphigoid, cardiomyopathy, Castleman disease, celiac disease, Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, congenital heart block, coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic fasciitis, erythema nodosum, experimental allergic encephalomyelitis, Evans syndrome, fibromyalgia, fibrosing alveolitis, giant cell arteritis (temporal arteritis), glomerulonephritis, goodpasture's syndrome, granulomatosis with polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, hypergammaglobulinemia, idiopathic thrombocytopenic purpura (ITP), IgA nephropathy, IgG4-related sclerosing disease, immunoregulatory lipoproteins, inclusion body myositis, inflammatory bowel disease, insulin-dependent diabetes (type 1), interstitial cystitis, juvenile arthritis, juvenile diabetes, Kawasaki syndrome, Lambert-Eaton syndrome, leukocytoclastic vasculitis, lichen planus, lichen sclerosus, ligneous conjunctivitis, linear IgA disease (LAD), lupus (SLE), lyme disease, Meniere's disease, microscopic polyangiitis, mixed connective tissue disease (MCTD), monoclonal gammopathy of undetermined significance (MGUS), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynauds phenomenon, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/Giant cell arteritis, thrombocytopenic purpura (TTP), Tolosa-Hunt syndrome, transverse myelitis, ulcerative colitis, undifferentiated connective tissue disease (UCTD), uveitis, vasculitis, vesiculobullous dermatosis, vitiligo, Waldenstrom's macroglobulinemia (WM), and Wegener's granulomatosis (Granulomatosis with Polyangiitis (GPA)).

In a particular embodiment, the autoimmune disease is selected from the group consisting of rheumatoid arthritis, type 1 diabetes, systemic lupus erythematosus (lupus or SLE), myasthenia gravis, multiple sclerosis, scleroderma, Addison's Disease, bullous pemphigoid, pemphigus vulgaris, Guillain-Barré syndrome, Sjogren syndrome, dermatomyositis, thrombotic thrombocytopenic purpura, hypergammaglobulinemia, monoclonal gammopathy of undetermined significance (MGUS), Waldenstrom's macroglobulinemia (WM), chronic inflammatory demyelinating polyradiculoneuropathy (CIDP), Hashimoto's Encephalopathy (HE), Hashimoto's Thyroiditis, Graves' Disease, Wegener's Granulomatosis, and antibody-mediated transplantation rejection (e.g., for tissue transplants such as renal transplant). In a particular embodiment, the autoimmune disease is type 1 diabetes, lupus, or rheumatoid arthritis.

As used herein, an "inflammatory disease" refers to a disease caused by or resulting from or resulting in inflammation. The term "inflammatory disease" may also refer to a dysregulated inflammatory reaction that causes an exaggerated response by macrophages, granulocytes, and/or T-lymphocytes leading to abnormal tissue damage and cell death. In a particular embodiment, the inflammatory disease comprises an antibody-mediated inflammatory process. An "inflammatory disease" can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's Syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroditis, Graves' disease, Goodpasture's disease, mixed connective tissue disease, sclerosing cholangitis, inflammatory bowel disease, Crohn's Disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, and vulvovaginitis, angitis, chronic bronchitis, osteomylitis, optic neuritis, temporal arteritis, transverse myelitis, necrotizing fasciitis, and necrotizing enterocolitis. In a particular embodiment, the inflammatory disease is selected from the group consisting of atherosclerosis, arteriosclerosis, autoimmune disorders, multiple sclerosis, systemic lupus erythematosus, rheumatoid arthritis, inflammatory arthritis, and myocarditis.

The instant invention also encompasses compositions and methods for the inhibition, treatment, and/or prevention of conditions or disorders associated with increased levels of a certain immunoglobulin in the blood serum such as hypergammaglobulinemia or monoclonal gammopathy of undetermined significance.

In another embodiment of the instant invention, Rho B inhibitors, e.g., anti-RhoB antibody, are administered to a subject to treat cancers sustained by antibody secretion. In a particular embodiment, the cancer is a blood tumor such as multiple myeloma. In another embodiment, the cancer is a solid tumor. Without being bound by theory, the antibody secretion may contribute to supportive inflammatory processes. Preclinical studies show that RhoB supports tumor angiogenesis and lymphangiogenesis that are vital for malignant progression, which has been demonstrated to rely upon antibody deposition in the inflammatory tumor microenvironment. Thus, anti-RhoB may be used to limit progression of primary tumors after treatment to prevent relapses and prolong remission. Anti-RhoB therapy may also be administered to a subject to treat antibody-mediated paraneoplastic syndromes that are associated with certain types of cancer. Examples include, without limitation, stiff-man syndrome, opsoclonus-myoclonus (e.g., in breast cancer), peripheral encephalomyelitis, and retinopathy (e.g., in lung cancer).

The methods of the instant invention also encompass the administration of at least one other agent for the treatment of autoimmune and/or inflammatory disease. Without being bound by theory, the administration of anti-RhoB antibodies blunts the production of autoimmune antibodies. As such, this technology does not displace disease-specific approaches for the treatment of the autoimmune disease.

In a particular embodiment, the method comprises administering at least one immunosuppressant. The terms "immunosuppressant" and "immunosuppressive agent", as used herein, include compounds or compositions which suppress immune responses or the symptoms associated therewith. Immunosuppressant include, without limitation, purine analogs (e.g., azathioprine), methotrexate, cyclosporine (e.g., cyclosporin A), cyclophosphamide, leflunomide, mycophenolate (mycophenolate mofetil), steroids (e.g., glucocorticoid, corticosteroid), methylprednisone, prednisone, non-steroidal anti-inflammatory drug (NSAID), chloroquine, hydroxycloroquine, chlorambucil, CD20 antagonist (e.g., rituximab, ocrelizumab, veltuzumab or ofatumumab), abatacept, a TNF antagonist (e.g., infliximab, adalimumab, etanercept), macrolides (e.g., pimecrolimus, tacrolimus (FK506), and sirolimus), dehydroepiandrosterone, lenalidomide, a CD40 antagonist (e.g., anti-CD40L antibodies), abetimus sodium, BLys antagonists (e.g., anti-BLyS (e.g., belimumab), dactinomycin, bucillamine, penicillamine, leflunomide, mercaptopurine, pyrimidine analogs (e.g., cytosine arabinoside), mizoribine, alkylating agents (e.g., nitrogen mustard, phenylalanine mustard, buslfan, and cyclophosphamide), folic acid antagonsists (e.g., aminopterin and methotrexate), antibiotics (e.g., rapamycin, actinomycin D, mitomycin C, puramycin, and chloramphenicol), human IgG, antilymphocyte globulin (ALG), antibodies (e.g., anti-CD3 (OKT3), anti-CD4 (OKT4), anti-CD5, anti-CD7, anti-IL-2 receptor (e.g., daclizumab and basiliximab), anti-alpha/beta TCR, anti-ICAM-1, muromonab-CD3, anti-IL-12, alemtuzumab and antibodies to immunotoxins), 1-methyltryptophan, and derivatives and analogs thereof. In a particular embodiment, the immunosuppressant is selected from the group consisting of methotrexate, hydroxychloroquine, CD20 antagonist (e.g., rituximab, ocrelizumab, veltuzumab or ofatumumab), abatacept, a TNF antagonist (e.g., infliximab, adalimumab, etanercept), sirolimus, and BLyS antagonists (e.g., anti-BLyS (e.g., belimumab)). In a particular embodiment, the immunosuppressant is a CD20 antagonists, TNF antagonist, or BLyS antagonist.

In a particular embodiment, the methods of the instant invention comprise administering at least one anti-inflammatory agent. As used herein, an "anti-inflammatory agent" refers to compounds for the treatment of an inflammatory disease or the symptoms associated therewith. Anti-inflammatory agents include, without limitation, non-steroidal anti-inflammatory drugs (NSAIDs; e.g., aspirin, ibuprofen, naproxen, methyl salicylate, diflunisal, indomethacin, sulindac, diclofenac, ketoprofen, ketorolac, carprofen, fenoprofen, mefenamic acid, piroxicam, meloxicam, methotrexate, celecoxib, valdecoxib, parecoxib, etoricoxib, and nimesulide), corticosteroids (e.g., prednisone, betamethasone, budesonide, cortisone, dexamethasone, hydrocortisone, methylprednisolone, prednisolone, tramcinolone, and fluticasone), rapamycin (see, e.g., Migita et al., Clin. Exp. Immunol. (1997) 108:199-203; Migita et al., Clin. Exp. Immunol. (1996) 104:86-91; Foroncewicz et al., Transpl. Int. (2005) 18:366-368), high density lipoproteins (HDL) and HDL-cholesterol elevating compounds (see, e.g., Birjmohun et al. (2007) Arterioscler. Thromb. Vasc. Biol., 27:1153-1158; Nieland et al. (2007) J. Lipid Res., 48:1832-1845; Bloedon et al. (2008) J. Lipid Res., Samaha et al. (2006) Arterioscler. Thromb. Vasc. Biol., 26:1413-1414, which discloses the use of rosiglitazone as an anti-inflammatory, Duffy et al. (2005) Curr. Opin. Cardiol., 20:301-306), rho-kinase inhibitors (see, e.g., Hu, E. (2006) Rec. Patents Cardiovasc. Drug Discov., 1:249-263), anti-malarial agents (e.g., hydroxychloroquine and chloroquine), acetaminophen, glucocorticoids, steroids, beta-agonists, anticholinergic agents, methyl xanthines, gold injections (e.g., sodium aurothiomalate), sulphasalazine, penicillamine, antiangiogenic agents, dapsone, psoralens, anti-viral agents, statins (see, e.g., Paraskevas et al. (2007) Curr. Pharm. Des., 13:3622-36; Paraskevas, K. I. (2008) Clin. Rheumatol. 27:281-287), and antibiotics (e.g., tetracyclines). In a particular embodiment, the anti-inflammatory is a statin or high density lipoproteins (HDL) and HDL-cholesterol elevating compound.

Figure 5:
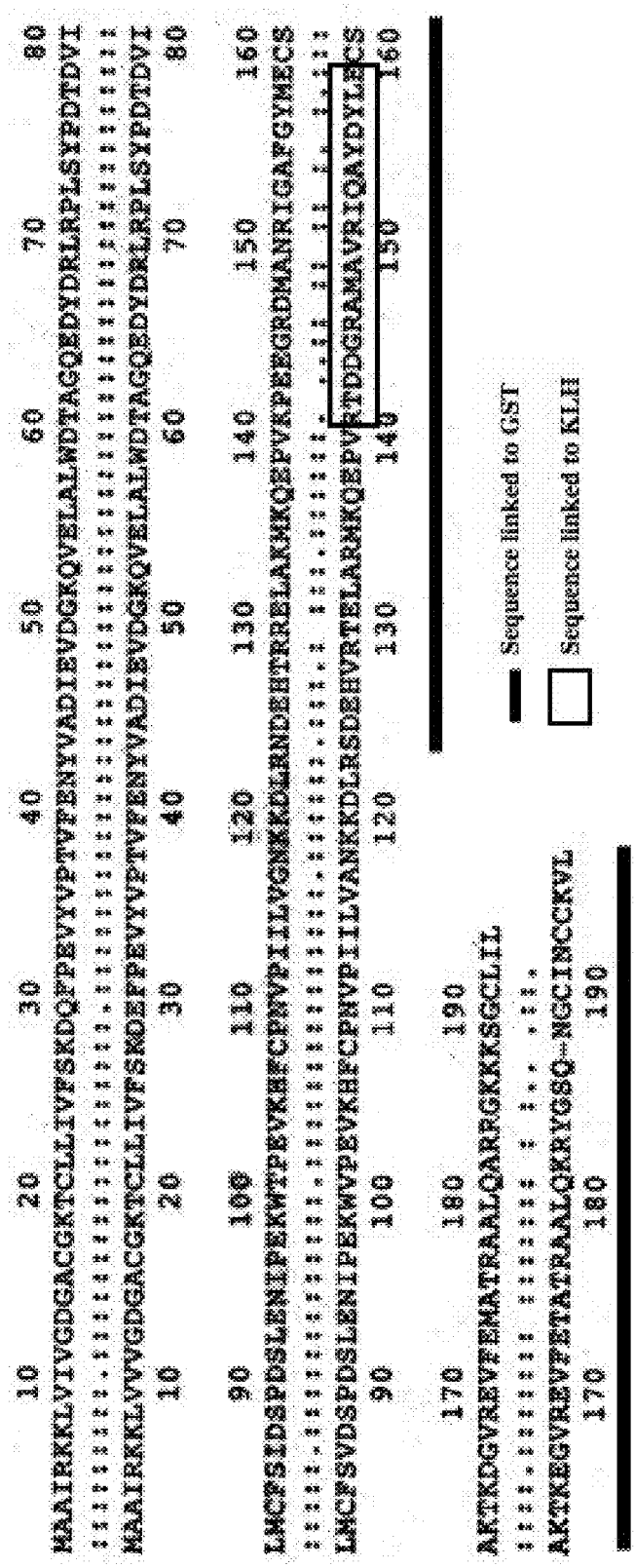
FIG. 5 provides a sequence alignment of RhoA (SEQ ID NO: 4) and RhoB (SEQ ID NO: 3). The underlined sequences and the boxed sequences represent antigens for RhoB antibodies.

In accordance with another aspect of the instant invention, RhoB peptides are provided. In a particular embodiment, the RhoB peptide comprises at least 10 consecutive amino acids of SEQ ID NO: 3. In a particular embodiment, the RhoB peptide comprises the C-terminal half (98 amino acids) of RhoB. In a particular embodiment, the RhoB peptide is selected from the group consisting of VANKKDLRSDE-HVRTELARMKQEPVRTDDGRAMAVRIQAYDYLEC-SAKTKEGVREVF ETATRAALQKRYGSQNGCINC-CKVL (SEQ ID NO: 5), KDLRSDEHVRTELARMKQEPVRTDDGRA-MAVRIQAYDYLECSAKTKEGVREVFETAT RAAL (SEQ ID NO: 6), SDEHVRTELARMKQEPVRTDDGRA-MAVRIQAYDYLECSAKTKEGVREVFETATRAAL QKRYGSQNGCINCCKVL (SEQ ID NO: 7), DDGRA-MAVRIQAY (SEQ ID NO: 2), RTDDGRAMAVRIQAY-DYLE (SEQ ID NO: 1), and AVRIQAYDYLE (SEQ ID NO: 8) (see, e.g., FIG. 5). The RhoB peptides may be longer or shorter than the above identified sequences by 0, 1, 2, 3, 4, 5, 6, 7, 8, 9, 10, or more amino acids, particularly 1, 2, 3, 4, or 5 amino acids, at the N-terminus and/or C-terminus of the peptide. In another embodiment, the peptides of the instant invention have at least 90%, 95%, 97%, 99%, or 100% homology or identity with SEQ ID NO: 3 (or SEQ ID NOs: 1, 2, 5-8).

The peptides of the present invention may be prepared in a variety of ways, according to known methods. The peptides of the instant invention may be made by chemical peptide synthesis (e.g., solid phase synthesis). The availability of nucleic acid molecules encoding the peptide also enables production of the protein using in vitro expression methods and cell-free expression systems known in the art. In vitro transcription and translation systems are commercially available, e.g., from Promega Biotech (Madison, Wis.) or Gibco-BRL (Gaithersburg, Md.). The peptides may also be produced by expression in a suitable prokaryotic or eukaryotic system. For example, part or all of a DNA molecule encoding for the peptide may be inserted into a plasmid vector adapted for expression in a bacterial cell, such as E. coli. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences. The peptides produced by gene expression in a recombinant prokaryotic or eukaryotic system may be purified according to methods known in the art.

The peptides of the invention, prepared by the aforementioned methods, may be analyzed according to standard procedures. For example, such protein may be subjected to amino acid sequence analysis, according to known methods.

The peptides of the instant invention may be conjugated to a carrier protein (e.g., a macromolecular carrier). For example, the peptides may be used for in vivo immunization purposes. While animals may be immunized with free peptide, anti-peptide antibody titer may be boosted by coupling the peptide to a carrier. Examples of carriers include, without limitation, KLH (keyhole limpet hemocyanin), GST (glutathione-S-transferase), BSA (bovine serum albumin), cBSA (cationized bovine serum albumin), OVA (ovalbumin), LPH (*limulus polyphenus* hemocyanin), and TT (tetanus toxoid).

The instant invention also encompasses antibodies or antibody fragments which are immunologically specific for RhoB (e.g., SEQ ID NO: 3). The instant invention also encompasses antibodies or antibody fragments which are immunologically specific for amino acid sequences as set forth above. In a particular embodiment, the peptide has at least 90%, 95%, 97%, 99%, or 100% homology or identity with SEQ ID NOs: 1, 2, 5, 6, 7, or 8. The peptides may be longer or shorter than the above identified sequences by 0, 1, 2, 3, 4, 5, 6, 7, 8, 9, 10, or more amino acids, particularly 1, 2, 3, 4, or 5 amino acids, at the N-terminus and/or C-terminus of the peptide. In another embodiment, the peptides of the instant invention have at least 90%, 95%, 97%, 99%, or 100% homology or identity with SEQ ID NO: 3.

The antibody molecules of the invention may be prepared using a variety of methods known in the art. Polyclonal and monoclonal antibodies may be prepared as described in Current Protocols in Molecular Biology, Ausubel et al. eds. Antibodies may be prepared by chemical cross-linking, hybrid hybridoma techniques and by expression of recombinant antibody fragments expressed in host cells, such as bacteria or yeast cells.

In a particular embodiment, the antibody or antibody fragment is immunologically specific for SEQ ID NO: 1 or SEQ ID NO: 8. In a particular embodiment, the antibody is a monoclonal antibody, a pair of antibodies, or a group of antibodies. In a particular embodiment, the antibody is a monoclonal antibody comprising SEQ ID NOs: 10 and 12. In a particular embodiment, the antibody is a monoclonal antibody comprising SEQ ID NOs: 14 and 16.

The antibody may be a naturally occurring antibody or may be a synthetic or modified antibody (e.g., a recombinantly generated antibody; a chimeric antibody; a bispecific antibody; a humanized antibody; a camelid antibody; and the like). The antibody may comprise at least one purification tag. In a particular embodiment, the framework antibody is an antibody fragment. Antibody fragments include, without limitation, immunoglobulin fragments including, without limitation: single domain (Dab; e.g., single variable light or heavy chain domain), Fab, Fab', F(ab')$_2$, and F(v); and fusions (e.g., via a linker) of these immunoglobulin fragments including, without limitation: scFv, scFv$_2$, scFv-Fc, minibody, diabody, triabody, and tetrabody. The antibody may also be a protein (e.g., a fusion protein) comprising at least one antibody or antibody fragment. In a particular embodiment of the instant invention, the antibody comprises an Fc region.

The antibody and antibody fragment of the instant invention may comprise at least one domain from the anti-RhoB monoclonal antibodies 7F7 and 9G5. For example, the antibody or antibody fragment may comprise at least one, two, three, four, five, or all six CDR domains the anti-RhoB monoclonal antibodies 7F7 and 9G5 (see FIGS. 9 and 10). In a particular embodiment, the antibody or antibody fragment comprises at least one or both of the CDR3 domains. In a particular embodiment, the domains of the antibody or antibody fragment have at least 90%, 95%, 97%, 99%, or 100% homology or identity with the domains present in the anti-RhoB monoclonal antibody 7F7 or 9G5. The domains may be longer or shorter than the domains depicted in FIGS. 9 and 10 by about 1, 2, 3, 4, or 5, amino acids, particularly 1 or 2 amino acids, at the N-terminus and/or C-terminus of the domain.

The antibody may also be a synthetic protein which mimics an immunoglobulin. Examples include, without limitation, Affibody® molecules (Affibody, Bromma, Sweden), darpins (designed ankyrin repeat proteins; Kawe et al. (2006) J. Biol. Chem., 281:40252-40263), and peptabodies (Terskikh et al. (1997) PNAS 94:1663-1668).

The antibodies of the instant invention may be further modified. For example, the antibodies may be humanized. In a particular embodiment, the hybrid antibodies (or a portion thereof) are inserted into the backbone of an antibody or antibody fragment construct. For example, the variable light domain and/or variable heavy domain of the antibodies of the instant invention may be inserted into another antibody construct. Methods for recombinantly producing antibodies are well-known in the art. Indeed, commercial vectors for certain antibody and antibody fragment constructs are available.

The antibodies of the instant invention may also be conjugated/linked to other components. For example, the antibodies may be operably linked (e.g., covalently linked, optionally, through a linker) to at least one detectable agent, imaging agent, contrast agent, immunosuppressant, or anti-inflammatory agent. The antibodies of the instant invention may also comprise at least one purification tag (e.g., a His-tag).

Compositions comprising the RhoB inhibitors or antibodies are also encompassed by the instant invention. In a particular embodiment, the composition comprises at least one antibody or antibody fragment of the instant invention and at least one pharmaceutically acceptable carrier.

The antibody molecules of the invention may be prepared using a variety of methods known in the art. Antibodies may be prepared by chemical cross-linking, hybrid hybridoma techniques and by expression of recombinant antibody or antibody fragments expressed in host cells, such as mammalian cells, bacteria or yeast cells. In one embodiment of the invention, the antibody molecules are produced by expression of recombinant antibody or antibody fragments in host cells. The nucleic acid molecules encoding the antibody may be inserted into expression vectors and introduced into host cells. The resulting antibody molecules are then isolated and purified from the expression system. The antibodies optionally comprise a purification tag by which the antibody can be purified.

The purity of the antibody molecules of the invention may be assessed using standard methods known to those of skill in the art, including, but not limited to, ELISA, immuno-histochemistry, ion-exchange chromatography, affinity chromatography, immobilized metal affinity chromatography (IMAC), size exclusion chromatography, polyacrylamide gel electrophoresis (PAGE), western blotting, surface plasmon resonance and mass spectroscopy.

The instant invention also encompasses hybridomas that secrete monoclonal RhoB antibodies. Presently, RhoB hybridomas are—on average—slow growing and produce lower quantities of antibody compared to other hybridomas. Several approaches may be taken to circumvent this possible limitation. For example, the nucleotide sequence of the anti-RhoB antibody may be cloned from the hybridomas and then anti-RhoB antibodies may be produced through molecular biological approaches. In another embodiment, RhoB-independent secreting hybridomas may be developed or hybridoma culture conditions may be modified to maximize antibody production.

The instant invention also encompasses methods for identifying small molecule or other molecular entities such as small nucleic acids, peptides, carbohydrates, and the like that are RhoB inhibitors. In a particular embodiment, the RhoB antibodies of the instant invention or fragments thereof (particularly the CDR regions) or corresponding epitopes may be used to design RhoB inhibitors with similar biologic activity.

DEFINITIONS

A "therapeutically effective amount" of a compound or a pharmaceutical composition refers to an amount effective to prevent, inhibit, treat, or lessen the symptoms of a particular disorder or disease. The treatment of an inflammatory disorder herein may refer to curing, relieving, and/or preventing the inflammatory disorder, the symptom of it, or the predisposition towards it.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, excipient, auxilliary agent or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described, for example, in "Remington's Pharmaceutical Sciences" by E. W. Martin.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions of an immunoglobulin molecule, and fusions of immunologically active portions of an immunoglobulin molecule.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

As used herein, the term "prevent" refers to the prophylactic treatment of a subject who is at risk of developing a condition resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc.

As used herein, the terms "host," "subject," and "patient" refer to any animal, including humans.

The phrase "small, interfering RNA (siRNA)" refers to a short (typically less than 30 nucleotides long, particularly 12-30 or 20-25 nucleotides in length) double stranded RNA molecule. Typically, the siRNA modulates the expression of a gene to which the siRNA is targeted. Methods of identifying and synthesizing siRNA molecules are known in the art (see, e.g., Ausubel et al. (2006) Current Protocols in Molecular Biology, John Wiley and Sons, Inc). As used herein, the term siRNA may include short hairpin RNA molecules (shRNA). Typically, shRNA molecules consist of short complementary sequences separated by a small loop sequence wherein one of the sequences is complimentary to the gene target. shRNA molecules are typically processed into an siRNA within the cell by endonucleases. Exemplary modifications to siRNA molecules are provided in U.S. Application Publication No. 20050032733. Expression vectors for the expression of siRNA molecules preferably employ a strong promoter which may be constitutive or regulated. Such promoters are well known in the art and include, but are not limited to, RNA polymerase II promoters, the T7 RNA polymerase promoter, and the RNA polymerase III promoters U6 and H1 (see, e.g., Myslinski et al. (2001) Nucl. Acids Res., 29:2502 09).

"Antisense nucleic acid molecules" or "antisense oligonucleotides" include nucleic acid molecules (e.g., single stranded molecules) which are targeted (complementary) to a chosen sequence (e.g., to translation initiation sites and/or splice sites) to inhibit the expression of a protein of interest. Such antisense molecules are typically between about 15 and about 50 nucleotides in length, more particularly between about 15 and about 30 nucleotides, and often span the translational start site of mRNA molecules. Antisense constructs may also be generated which contain the entire sequence of the target nucleic acid molecule in reverse orientation. Antisense oligonucleotides targeted to any known nucleotide sequence can be prepared by oligonucleotide synthesis according to standard methods.

Therapies and Compositions for the Treatment of Autoimmune and Inflammatory Diseases As stated hereinabove, the present invention encompasses compositions comprising at least one anti-RhoB antibody (including fragments thereof) and at least one pharmaceutically acceptable carrier. The composition may further comprise at least one other anti-inflammatory agent and/or at least one immunosuppressive agent. Alternatively, at least one other anti-inflammatory agent and/or at least one immunosuppressive agent may be contained within a separate composition(s) with at least one pharmaceutically acceptable carrier. The composition(s) comprising at least one anti-RhoB antibody and the composition(s) comprising at least one other anti-inflammatory agent and/or at least one immunosuppressive agent may be contained within a kit. Such composition(s) may be administered, in a therapeutically effective amount, to a patient in need thereof for the treatment of an inflammatory or autoimmune disease. In a particular embodiment, the patient is monitored at least once for the inflammatory or autoimmune disease after administration of the compositions of the instant invention to monitor the treatment of the inflammatory or autoimmune disease (e.g., in the case of rheumatoid arthritis, joint (e.g., hand joint) pain and/or stiffness; presence of rheumatoid nodules; and/or presence of rheumatoid factor or rheumatoid factor antibodies in the blood).

The compositions of the present invention can be administered by any suitable route, for example, by injection (e.g., for local or systemic administration), intravenous, oral, pulmonary, nasal or other modes of administration. In general, the pharmaceutically acceptable carrier of the composition is selected from the group of diluents, preservatives, solubilizers, emulsifiers, adjuvants and/or carriers. The compositions can include diluents of various buffer content (e.g., Tris-HCl, acetate, phosphate), pH and ionic strength; and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of polymeric compounds such as polylactic acid, polyglycolic acid, etc., or into liposomes or nanoparticles. Such compositions may influence the physical state, stability, rate of in vivo release, and rate of in vivo clearance of components of a pharmaceutical composition of the present invention. See, e.g., Remington's Pharmaceutical Sciences, 18th Ed. (1990, Mack Publishing Co., Easton, Pa. 18042) pages 1435-1712 which are herein incorporated by reference. The pharmaceutical composition of the present invention can be prepared, for example, in liquid form, or can be in dried powder form (e.g., lyophilized).

In yet another embodiment, the pharmaceutical compositions of the present invention can be delivered in a controlled release system, such as using an intravenous infusion, an implantable osmotic pump, a transdermal patch, liposomes, or other modes of administration. In a particular embodiment, a pump may be used (see Langer, supra; Sefton, CRC Crit. Ref. Biomed. Eng. (1987) 14:201; Buchwald et al., Surgery (1980) 88:507; Saudek et al., N. Engl. J. Med. (1989) 321:574). In another embodiment, polymeric materials may be employed (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. (1983) 23:61; see also Levy et al., Science (1985) 228:190; During et al., Ann. Neurol. (1989) 25:351; Howard et al., J. Neurosurg. (1989) 71:105). In yet another embodiment, a controlled release system can be placed in proximity of the target tissues of the animal, thus requiring only a fraction of the systemic dose (see, e.g., Goodson, in Medical Applications of Controlled Release, supra, (1984) vol. 2, pp. 115-138). In particular, a controlled release device can be introduced into an animal in proximity to the site of inappropriate inflammation. Other controlled release systems are discussed in the review by Langer (Science (1990) 249:1527-1533).

The methods of the instant invention may further comprise the administration of at least one other therapeutic method for the treatment of the autoimmune disease or inflammatory disease. For example, in the treatment of an autoimmune disease, the anti-RhoB antibody may be co-administered with radiation of the subject's lymph nodes or with plasmapheresis.

In yet another embodiment, the present invention encompasses compositions comprising at least one RhoB sequence peptide (including sequences thereof) and at least one pharmaceutically acceptable carrier. The composition may further comprise other agents (e.g., at least one other anti-inflammatory agent and/or at least one immunosuppressive agent) or be included in a kit with another composition, as described hereinabove for the anti-RhoB antibodies. The compositions may be delivered to a subject (e.g., therapeutic methods) as described hereinabove for the anti-RhoB antibodies.

The following examples are provided to illustrate various embodiments of the present invention. The examples are not intended to limit the invention in any way.

EXAMPLE 1

RhoB-knockout mice were immunized with RhoB-peptide-KLH or KLH (keyhole limpet hemocyanin). Specifically, at Day 0, RhoB-KO mice were injected with RhoB-peptide-KLH or KLH in complete Freund's adjuvant (CFA). At Day 14, a booster injection was given with RhoB-peptide-KLH or KLH in incomplete Freund's adjuvant (IFA). Lastly, a second booster injection was administered at Day 29 with RhoB-peptide-KLH or KLH in phosphate buffered saline (PBS). Bleeds were obtained at Day 10 and Day 24 and serum was harvested at Day 32.

K/BxN TCR transgenic mice express a TCR reactive to a self-peptide derived from the glucose-6-phosphate isomerase (GPI), presented by the MHC class II molecule $A^{g7}$ (Korganow et al. (1999) Immunity, 10:451-461; Kouskoff et al. (1996) Cell, 87:811-822; Matsumoto et al. (1999) Science, 286:1732-1735). K/BxN mice spontaneously develop a very aggressive form of arthritis at 4 to 5 weeks of age. The arthritis of the K/BxN mice mimics arthritis in humans in that it is chronic, progressive, symmetrical, and exhibits the same histological features of human arthritis. The arthritis experienced by K/BxN mice is joint specific and allows for the scoring of the arthritis by caliper measurement of ankle thickness (Korganow et al. (1999) Immunity, 10:451-461; Ji et al. (2001) J. Exp. Med., 194:321-330).

K/BxN mice (5 mice per group) were treated with 1) saline, 2) anti-KLH serum, or 3) anti-RhoB-peptide serum. Specifically, serum (200 µl) was administered i.p. to 21 day old mice. Mean ankle thickness was measured over time as an indicator arthritis. As seen in FIG. 1, RhoB anti-serum inhibits arthritis.

Figure 2A:
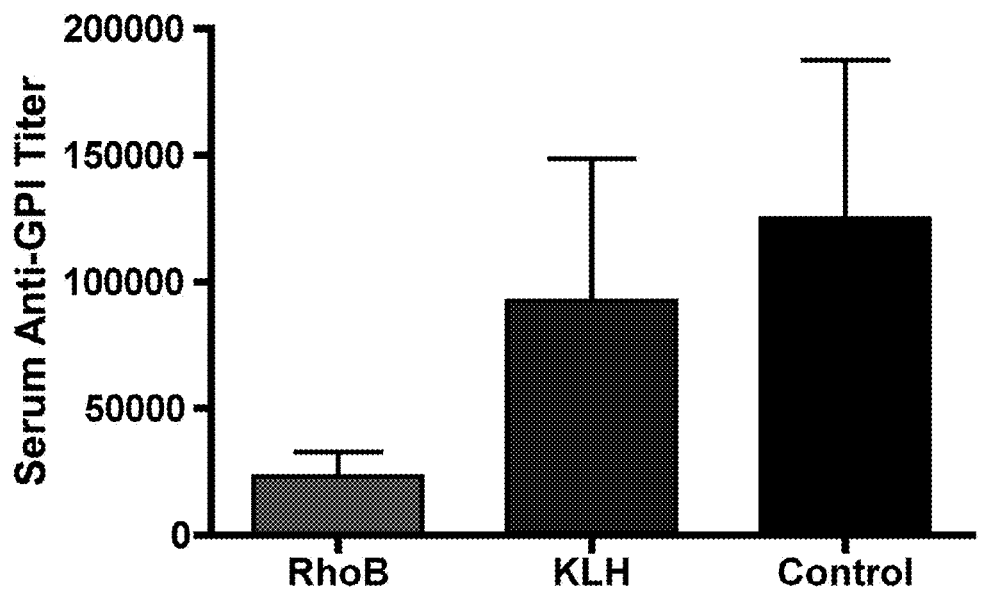
FIG. 2A is a graph of the titer of serum anti-glucose-6-phosphate isomerase (GPI) Ig from K/BxN mice treated with anti-RhoB-peptide serum, anti-KLH serum, or carrier alone.
Figure 2B:
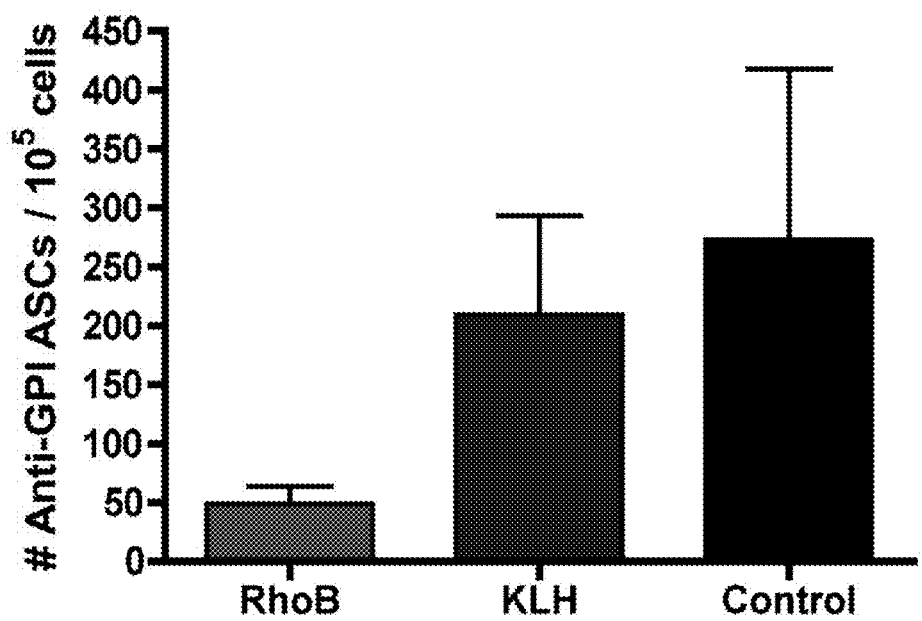
FIG. 2B is a graph of the number of anti-GPI secreting cells per $10^5$ cells of K/BxN mice treated with anti-RhoB-peptide serum, anti-KLH serum, or carrier alone.

K/BxN mice produce arthritogenic Abs directed against GPI, which develop at high titers because of the preferential help that B cells expressing GPI-specific immunoglobulins receive from GPI-reactive T cells displaying the transgene-encoded TCR. As above, K/BxN mice (5 mice per group) were treated with a total of 200 µl (100 µl of serum mixed with 100 µl saline) (i.p.) of 1) saline, 2) anti-KLH serum, or 3) anti-RhoB-peptide serum. As seen in FIGS. 2A and 2B, the serum of K/BxN mice administered with RhoB anti-serum had reduced levels of serum anti-GPI Ig (as determined by enzyme-linked immunosorbent assay (ELISA)) compared to K/BxN mice administered with KLH anti-serum or carrier alone and reduced numbers of anti-GPI antibody secreting cells (as determined by enzyme-linked immunosorbent spot (ELISPOT)) compared to K/BxN mice administered with KLH anti-serum or carrier alone.

In addition to the above, it was also determined whether RhoB anti-serum affected other cytokines in K/BxN mice. The administration of RhoB anti-serum to K/BxN mice did not significantly modulate the levels of IFNγ, TNFα, IL-6, IL-10, MCP-1, MIP-1α, MIP-1β, or RANTES compared to K/BxN mice administered with KLH anti-serum or carrier alone.

Splenocytes were isolated from the mice and B cells were fused with immortalized myeloma cells (Sp2/0) to generate hybridomas. 48 samples were tested. 7 yielded strong positives to Peptide 1 (RTDDGRAMAVRIQAYDYLE; SEQ ID NO: 1; amino acids 140-158 of human RhoB (GenBank Accession No. CAA29968)) and 5 yielded positives to Peptide 1 and Peptide 2 (DDGRAMAVRIQAY; SEQ ID NO: 2; amino acids 142-154 of human RhoB (GenBank Accession No. CAA29968)).

FIG. 3 provides the amino acid sequence of human RhoB. Peptide 1 is underlined. Mice vaccinated with a peptide antigen encompassing this sequence were divided into two sets of antibodies. These two sets are defined by slightly different but overlapping epitopes: binding of one set of antibodies may be affected by Y156 phosphorylation, but the other set of antibodies would not likely be (see above results distinguishing between Peptide 1 and Peptide 2, which lacks the tyrosine at 156). Both sets of antibodies specifically recognize full-length RhoB protein, but only one blocked antibody secretion by B cells in tissue culture or in animals.

Figure 4:
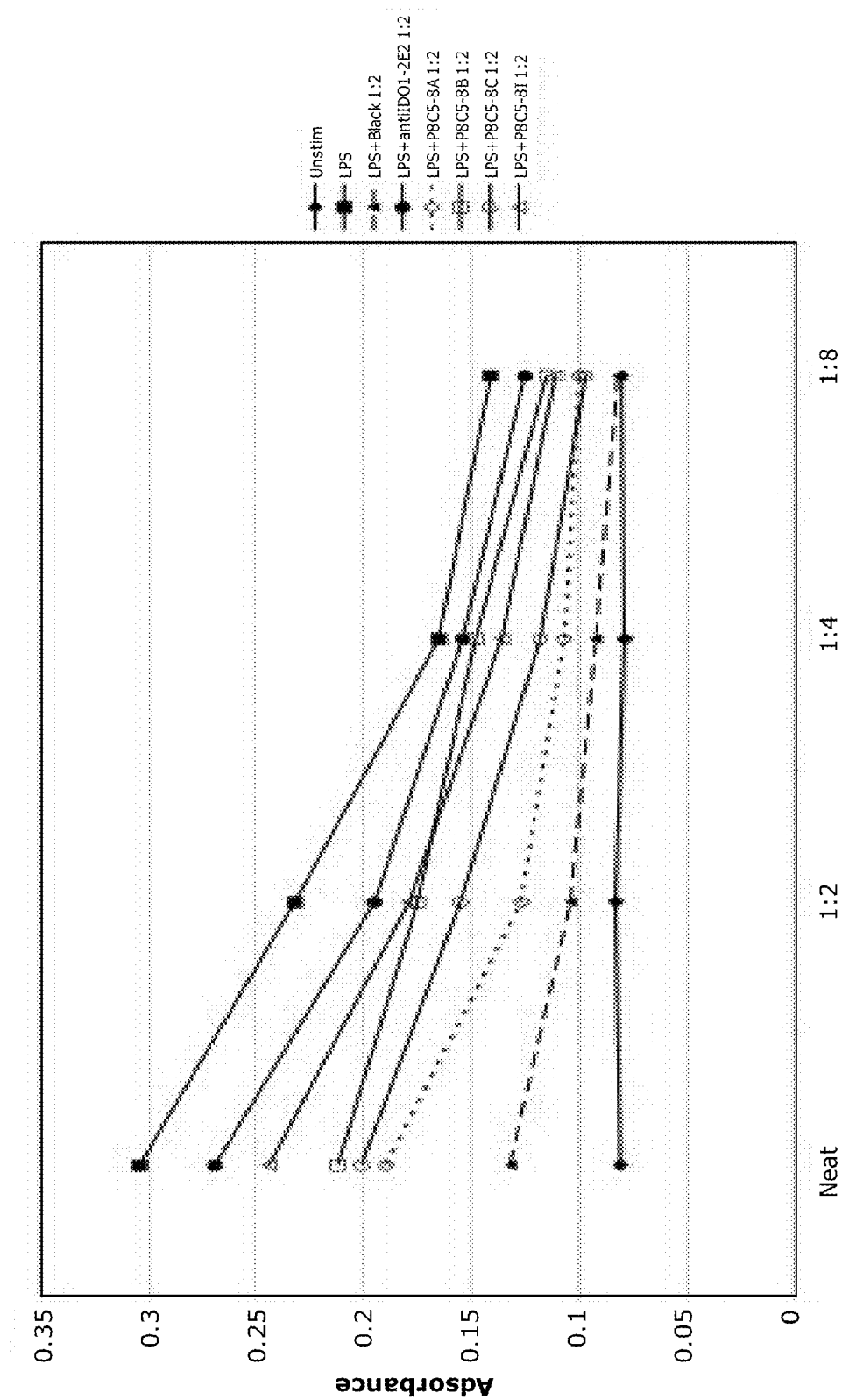
FIG. 4 provides a graph of the IgM secretion with or without lipopolysaccharide (LPS) stimulation in the presence or absence of a control antibody or anti-RhoB antibodies from a hybridoma or a subclone thereof.

FIG. 4 provides the results of an ELISA experiment where an anti-RhoB hybridoma supernatant (Black) is demonstrated to suppress antibody secretion by LPS-treated mouse B cells: compare the baseline (unactivated; diamond), activated red line (square), and suppressed line (triangle). The X line is a non-specific control (IDO antibody) that does not suppress activation. The other lines represent supernatants obtained from anti-RhoB hybridoma subclones out of the original hybridoma, showing intermediate levels of suppression. Propidium iodide (PI) staining demonstrated that the B cells did proliferate in response to LPS. An analysis using an IL6 bead array showed that the anti-RhoB hybridomas were not secreting IL6.

EXAMPLE 2

Figure 6A:
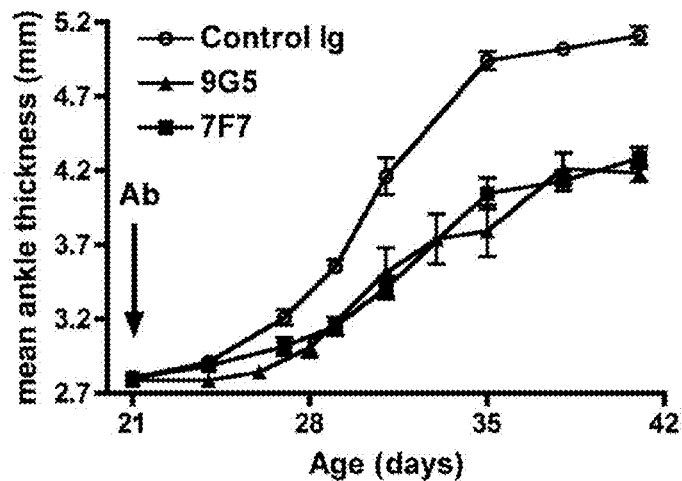
FIG. 6A provides a graph of rear ankle thickness ±SEM of K/BxN mice treated with anti-RhoB monoclonal antibody 9G5 or 7F7 or control Ig before the onset of arthritis (21 days of age).
Figure 6B:
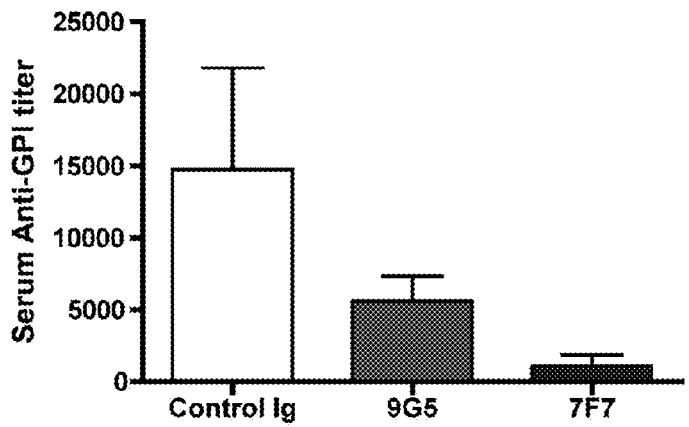
FIGS. 6B and 6C provide graphs of the anti-GPI autoantibody titers and the number of anti-GPI antibody secreting cells (ASCs) in the mice, respectively.
Figure 6C:
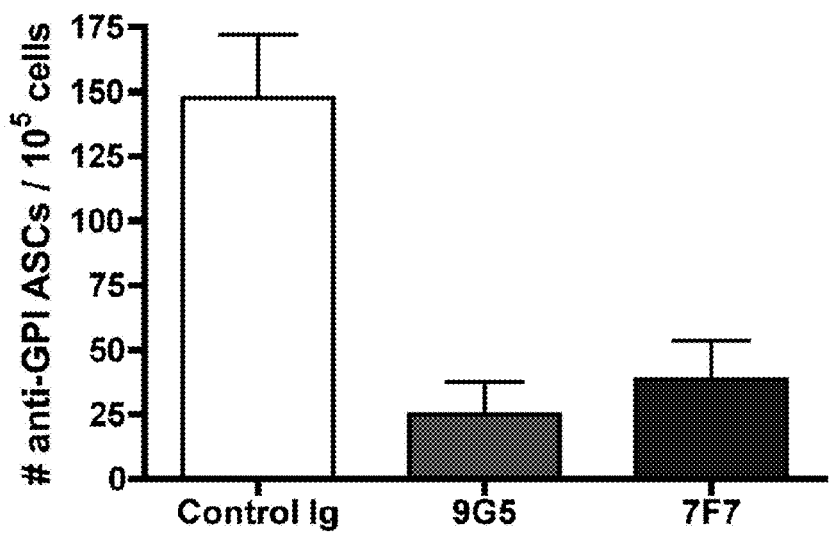

K/BxN mice were treated with 500 µg of anti-RhoB monoclonal antibodies 9G5 or 7F7 or control Ig before the onset of arthritis (21 days of age). FIG. 6A shows that both anti-RhoB monoclonal antibodies 9G5 and 7F7 inhibited arthritis as indicated by rear ankle thickness. FIGS. 6B and 6C show that the anti-RhoB monoclonal antibodies also inhibit autoantibody production as anti-GPI autoantibody titers were measured by ELISA (FIG. 6B) and anti-GPI antibody secreting cells (ASCs) were measured by ELISpot assay (FIG. 6C).

Figure 7A:
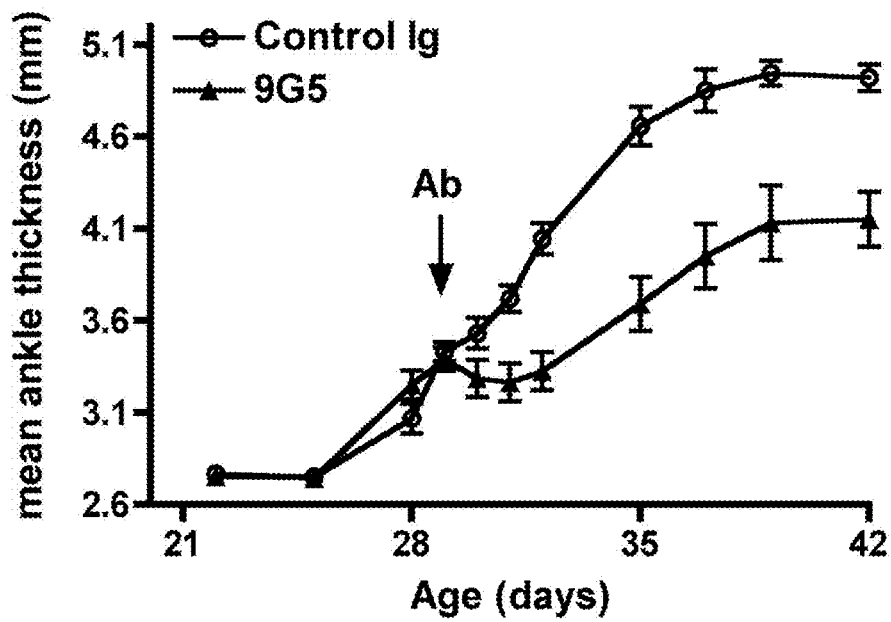
FIG. 7A provides a graph of the rear ankle thickness ±SEM of K/BxN mice over a long time course that were treated with anti-RhoB monoclonal antibody 9G5 or control Ig after the onset of arthritis at 4 weeks of age.
Figure 7B:
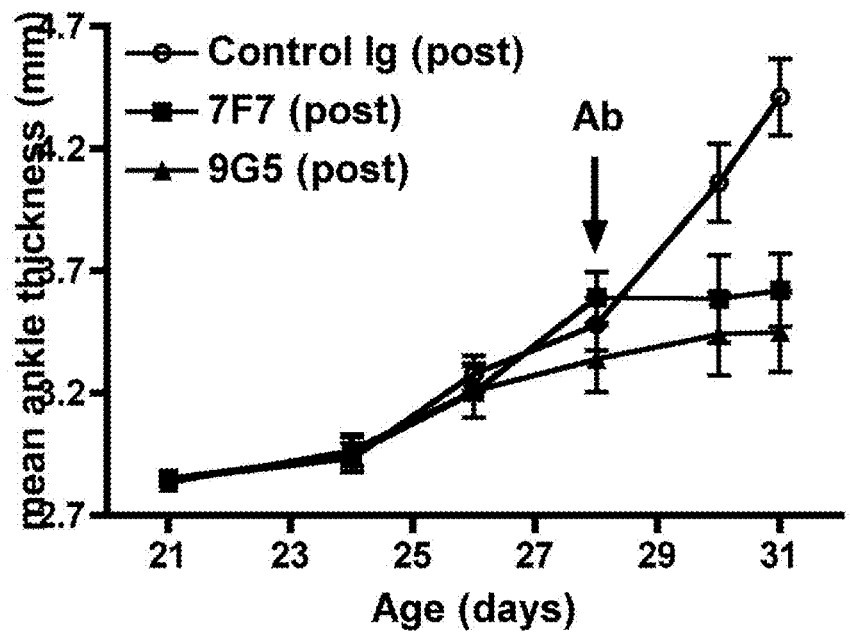
FIG. 7B provides a graph of the rear ankle thickness ±SEM of K/BxN mice over a shorter time course that were treated with anti-RhoB monoclonal antibody 9G5 or 7F7 or control Ig after the onset of arthritis at 4 weeks of age.

K/BxN mice were also treated with 500 µg of anti-RhoB monoclonal antibodies 9G5 or 7F7 or control Ig after the onset of arthritis (4 weeks of age). As seen in FIG. 7, anti-RhoB monoclonal antibodies 9G5 and 7F7 inhibited the progression of arthritis, as determined by rear ankle thickness.

In addition to the above, it was also determined whether anti-RhoB monoclonal antibodies affected other cytokines in K/BxN mice. K/BxN mice were treated with 500 µg 7F7 or control Ig at 21 days of age. Cells from the joint draining lymph nodes were harvested at 6 weeks of age and cultured overnight in PMA (50 ng/ml) with ionomycin (500 ng/ml). Cytokines were measured in culture supernatants by cytometric bead array. The administration of the anti-RhoB monoclonal antibody 7F7 to K/BxN mice did not significantly modulate the levels of the inflammatory cytokines IFNγ, TNFα, IL-17, IL-10, MCP-1, MIP-1α, MIP-1β, and RANTES or B-cell related cytokines IL-4, IL-5, IL-6, IL-9, IL-10, and IL-13 compared to K/BxN mice administered with control Ig.

Figure 8A:
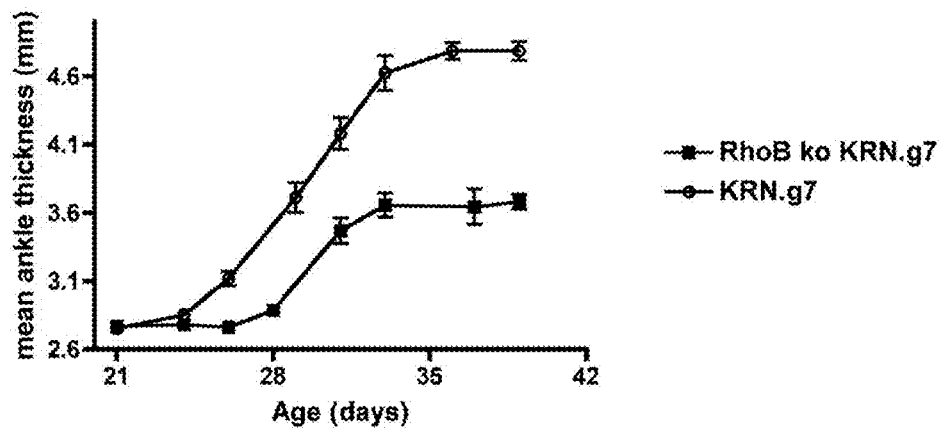
FIG. 8A provides a graph of rear ankle thickness ±SEM in arthritic RhoB KO mice (RhoB KO KRN.g7).
Figure 8B:
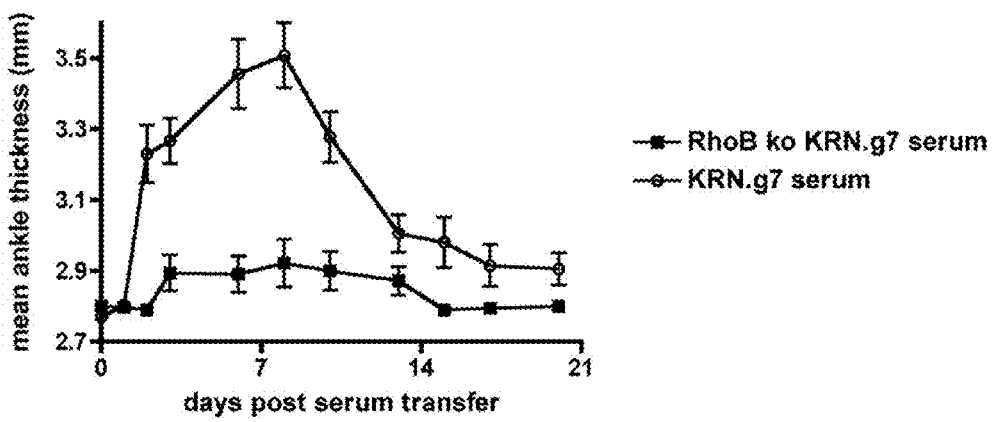
FIG. 8B provides a graph of rear ankle thickness ±SEM in naïve C57BL/6 mice that received a serum transfer from KRN B6.g7 or RhoB KO KRN B6.g7 mice on day 0.
Figure 8C:
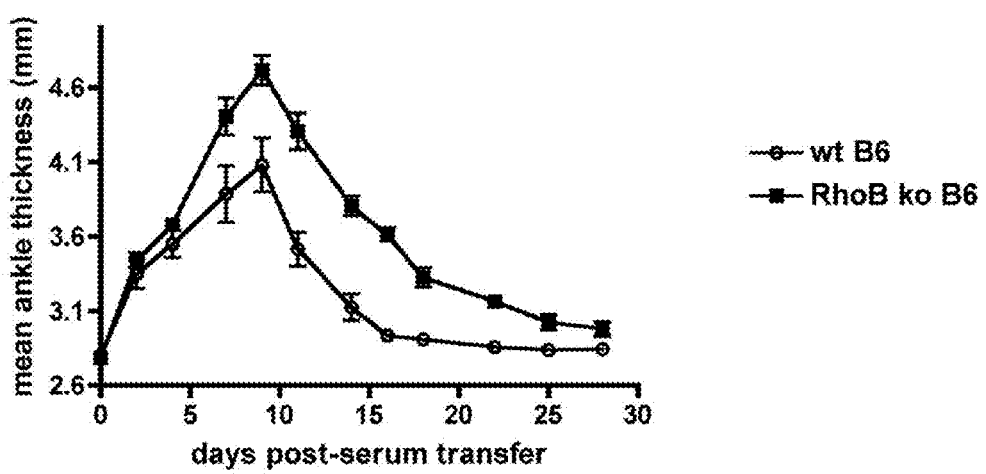
FIG. 8C provides a graph of rear ankle thickness ±SEM in naïve wild-type or RhoB KO C57BL/6 mice that received a serum transfer from arthritic K/BxN mice on day 0.

Arthritic RhoB knockout (KO) (RhoB KO KRN.g7) mice were generated by crossing onto the KRN.g7 background. KRN B6.g7 mice are C57BL/6 mice that express both the KRN TCR tg and the IAg7 MHC Class II molecule necessary for KRN T cell activation, but lack the rest of the NOD-associated genes (Kouskoff et al. (1996) Cell 87:811-822). FIG. 8A shows that RhoB KO mice had reduced arthritis compared to KRN.g7 mice, as determined by rear ankle thickness. FIG. 8B shows that serum from RhoB KO KRN.g7 mice was also unable to induce arthritis when transferred to naïve recipients. Specifically, serum from KRN B6.g7 or RhoB KO KRN B6.g7 mice was adoptively transferred into naïve C57BL/6 mice on day 0. However, FIG. 8C shows that arthritis can be induced in RhoB ko mice when arthritogenic K/BxN serum is adoptively transferred. Serum from arthritic K/BxN mice was adoptively transferred into naïve wt or RhoB KO C57BL/6 mice on day 0. Notably, the observed arthritis was more severe and of a longer duration with the RhoB KO mice. Without being bound by theory, the observed increased severity in arthritis in RhoB KO mice may be due to the inability of the mice to clear autoantibody. Indeed, anti-GPI autoantibody titers were moderately increased in RhoB KO KRN.g7 mice compared to KRN.g7 mice, but the number of anti-GPI antibody secreting cells (ASCs) were similar between the two mice.

Additionally, it was also determined whether cytokines were affected in RhoB KO mice. Cells from the joint draining lymph nodes were harvested at 6 weeks of age and cultured overnight in PMA (50 ng/ml) with ionomycin (500 ng/ml). Cytokines were measured in culture supernatants by cytometric bead array. When compared to KRN.g7 mice, RhoB KO KRN.g7 mice did not have significantly modulated levels of the inflammatory cytokines IFNγ, TNFα, IL-17, IL-10, and MCP-1 (although RANTES, MIP-1α, and MIP-1β trended slightly lower in RhoB KO KRN.g7 mice) or B-cell related cytokines IL-4, IL-5, IL-6, IL-9, IL-10, and IL-13. Without being bound by theory, the similarity in the mouse phenotypes of RhoB KO mice compared to mice administered an anti-RhoB antibody is further evidence that anti-RhoB antibodies exert their activity through their interaction with RhoB.

RhoB KO C57BL/6 mice also possessed normal lymphoid populations. Specifically, the percentage of lymphoid populations in bone marrow, thymus, spleen, lymph nodes, and peritoneal cavity from wild-type and RhoB KO C57BL/6 mice were measured by flow cytometry. Serum Ig levels from wild-type and RhoB KO C57BL/6 mice were also measured by ELISA. Notably, no significant difference in lymphoid populations or serum Ig levels (IgM, IgG1, IgG2b, IgG2c, and IgG3) was observed between wild-type and RhoB KO C57BL/6 mice. RhoB−/−, RhoB+/−, or RhoB+/+C57BL/6 mice were also immunized with 100 μg NP-KLH in alum on day 0. Serum samples were taken on days 0, 5, 14, and 21 and analyzed for anti-NP IgM or IgG by ELISA. The RhoB KO mice exhibited a normal response to immunization.

Several publications and patent documents are cited in the foregoing specification in order to more fully describe the state of the art to which this invention pertains. The disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated anti-RhoB antibody or fragment thereof which binds SEQ ID NO: 1 or 2.

2. An anti-RhoB antibody which comprises SEQ ID NOs: 10 and 12.

3. An anti-RhoB antibody which comprises SEQ ID NOs: 14 and 16.

4. A composition comprising at least one anti-RhoB antibody or fragment thereof of claim 1 and at least one pharmaceutically acceptable carrier.

5. The composition of claim 4, wherein said composition further comprises at least one anti-inflammatory agent.

6. The composition of claim 4, wherein said composition further comprises at least one immunosuppressant.

7. An isolated anti-RhoB antibody or fragment thereof, wherein said antibody or fragment thereof comprises all six complementarity-determining regions (CDRs) of an anti-RhoB antibody comprising SEQ ID NOs: 10 and 12 or an anti-RhoB antibody comprising SEQ ID NOs: 14 and 16.

* * * * *